US010570177B2

(12) United States Patent
Chan et al.

(10) Patent No.: US 10,570,177 B2
(45) Date of Patent: Feb. 25, 2020

(54) P3 PEPTIDYLIC INHIBITORS FOR TREATING CAG-REPEAT RNA TOXICITY IN POLYGLUTAMINE DISEASES

(71) Applicants: The Chinese University of Hong Kong, Shatin, New Territories, Hong Kong (CN); UNIVERSITY OF COPENHAGEN, Copenhagen K (DK)

(72) Inventors: Ho Yin Edwin Chan, Hong Kong (CN); Knud J. Jensen, Copenhagen (DK); Jacky Chi Ki Ngo, Hong Kong (CN); Kasper K Sorensen, Smorum (DK); Qian Zhang, Hong Kong (CN); Zhong Zuo, Hong Kong (CN)

(73) Assignees: The Chinese University of Hong Kong, Shatin, N.T., Hong Kong (CN); University of Copenhagen, Copenhagen (DK)

( * ) Notice: Subject to any disclaimer, the term of this patent is extended or adjusted under 35 U.S.C. 154(b) by 0 days.

(21) Appl. No.: 15/895,877

(22) Filed: Feb. 13, 2018

(65) Prior Publication Data

US 2018/0251493 A1     Sep. 6, 2018

Related U.S. Application Data

(60) Provisional application No. 62/465,513, filed on Mar. 1, 2017.

(51) Int. Cl.
| | |
|---|---|
| A61K 38/10 | (2006.01) |
| A61K 38/00 | (2006.01) |
| A61K 45/06 | (2006.01) |
| A61K 38/17 | (2006.01) |
| A61K 51/08 | (2006.01) |
| C07K 14/47 | (2006.01) |
| C07K 7/08 | (2006.01) |
| C07K 7/06 | (2006.01) |
| A61P 25/28 | (2006.01) |

(52) U.S. Cl.
CPC ............... *C07K 7/08* (2013.01); *A61K 38/10* (2013.01); *A61K 45/06* (2013.01)

(58) Field of Classification Search
CPC ........ A61K 38/10; A61K 38/00; A61K 45/06; A61K 48/00; A61K 38/17; A61K 51/08; A61P 25/28; C07K 14/47; C07K 7/08; C07K 7/06
USPC ........................... 514/1.1, 21.5; 530/300, 327
See application file for complete search history.

(56) References Cited

U.S. PATENT DOCUMENTS

| | | | | |
|---|---|---|---|---|
| 4,966,848 A | * | 10/1990 | Smith | C12N 9/1029 435/193 |
| 5,223,421 A | * | 6/1993 | Smith | C12N 9/1029 435/193 |
| 5,837,218 A | * | 11/1998 | Peers | A61K 51/088 424/1.69 |
| 9,297,798 B2 | * | 3/2016 | Chan | G01N 33/6896 |
| 2014/0357578 A1 | * | 12/2014 | Chan | G01N 33/6896 514/21.5 |

OTHER PUBLICATIONS

UniProt L9L5A5 from UniProt, pp. 1-4. Integrated into UniProtKB/TrEMBL on Apr. 3, 2013.*
Lipidation from https://www.uniprot.org/help/lipid, pp. 1-3. Accessed May 21, 2019.*
Glycosylation from Thermo Fisher Scientific, pp. 1-10. Accessed Jan. 23, 2019.*
Yamamoto, A., "Improvement of Intestinal Absorptoin of Peptide and Protein Drugs by Chemical Modifications with Fatty Acids," Japanese Journal of Clinical Medicine, 1998, pp. 49-55. (in Japanese).*
Yamamoto, A., "Improvement of Intestinal Absorptoin of Peptide and Protein Drugs by Chemical Modifications with Fatty Acids," Japanese Journal of Clinical Medicine, Machine translation, 1998, pp. 1-17.*

* cited by examiner

*Primary Examiner* — Julie Ha
(74) *Attorney, Agent, or Firm* — Kilpatrick Townsend & Stockton LLP

(57) ABSTRACT

Herein provided are peptide inhibitors and methods for treating polyglutamine (polyQ) diseases. Also disclosed are related compositions and kits for therapeutic use in the treatment of polyQ diseases.

20 Claims, 9 Drawing Sheets
Specification includes a Sequence Listing.

P3 PEPTIDYLIC INHIBITORS FOR TREATING CAG-REPEAT RNA TOXICITY IN POLYGLUTAMINE DISEASES

RELATED APPLICATIONS

This application claims priority to U.S. Provisional Patent Application No. 62/465,513, filed Mar. 1, 2017, the contents of which are hereby incorporated by reference in the entirety for all purposes.

REFERENCE TO SUBMISSION OF A SEQUENCE LISTING AS A TEXT FILE

The Sequence Listing written in file 080015-021510US-1075196_SequenceListing.txt created on May 21, 2018, 14,211 bytes, machine format IBM-PC, MS-Windows operating system, is hereby incorporated by reference in its entirety for all purposes.

BACKGROUND OF THE INVENTION

Many neurodegenerative diseases, including Alzheimer's and Parkinson's diseases, are caused by protein misfolding. Cellular proteins that adopt abnormal pathogenic conformations oligomerize and subsequently form soluble and/or insoluble aggregates in cells causing neuronal dysfunction and death. Polyglutamine (polyQ) diseases belong to the protein misfolding disease group. It is now known that polyQ toxicity is attributed to the toxic gain-of-function nature of misfolded disease proteins that harbour the expanded polyQ domain. Unfolded protein response (UPR) is one inducible cellular protective pathway that responds to the emergence of misfolded proteins in cells. It has been reported that this mechanism is involved in neurodegenerative diseases, including polyglutamine-induced neurodegeneration. UPR can be mediated by the interaction between misfolded proteins in the endoplasmic reticulum and the molecular chaperone GRP78/BiP, and this interaction would cause the activation of UPR sensors, including activating transcription factor 6 (ATF6), inositol requiring 1 (IRE1) and PKR-like endoplasmic reticulum kinase (PERK). The induction of GRP78/BiP expression has been used as a reliable indicator of UPR. Upregulation of GRP78/Bip has been observed in polyQ degeneration, which clearly indicates the involvement of protein misfolding in polyQ pathogenesis. It is likely, however, that there are other mechanisms involved in polyQ diseases. In particular, the mRNA transcripts that encode the polyQ peptides can play a role in these diseases, especially when the mRNAs encode the polyQ portion as an expanded CAG triplet nucleotide repeat. Such expanded CAG-RNAs are known to contribute to cytotoxicity through mechanisms that are independent of polyQ-mediated cytotoxicity.

Accordingly, there is a continued need to develop new and effective methods and compositions for treating polyQ diseases by reducing or eliminating cytotoxicty induced by the expanded CAG-RNA molecules. This invention fulfills this and other related needs.

BRIEF SUMMARY OF THE INVENTION

It was previously reported that certain fragments of the nucleolin protein (NCL) can directly interact with CAG-repeat RNA and suppress CAG-repeat RNA toxicity, see, e.g., the P3 and P3L fragments described in U.S. Patent Application Publication No. 2014/0357578; and U.S. patent application Ser. No. 15/046,249. The present inventors have now discovered that modifications to NCL fragments can result in peptide variants that are surprisingly far more effective in their ability to suppress CAG-repeat RNA toxicity. Thus, this invention provides novel methods and compositions useful for treating a polyQ disease.

In the first aspect, the present invention provides an isolated polypeptide that is derived from the P3 fragment. The P3 variant comprises the amino acid sequence of SEQ ID NO:1, and the amino acid sequence has been modified, for example, deletion, addition, or substitution at one or more residues of SEQ ID NO:1, as well as chemical modification at the N- or C-terminus of SEQ ID NO:1 or at any of the side chains of any terminal or internal residues of SEQ ID NO:1. The polypeptide exhibits a binding affinity to an RNA comprising multiple CAG repeats (e.g., more than 10, 20, 50, 75, such as 78, CAG repeats) at least about twice as high as the binding affinity of SEQ ID NO:1 to the same RNA, in some cases at least about five times, or at least about ten times, or at least about twenty times, or at least about twenty-five times, or at least about fifty times higher than the binding affinity of SEQ ID NO:1 to the same RNA.

In some embodiments, the modification in the P3 variant comprises substitution and chemical modification at the N- and/or C-terminus of SEQ ID NO:1. In some embodiments, the modification comprises substitution at one or two amino acid residues within SEQ ID NO:1. In some embodiments, the modification comprises acetylation at the N-terminus and/or amidation at the C-terminus. In the case of variant P3V8, the modification comprises acetylation and lipidation at the N-terminus, where the amino acid sequence of SEQ ID NO:1 is modified by N-terminal acetylation and C-terminal amidation, optionally with further N-terminal lipidation by N-acylation with palmitic acid. Other examples of P3 variants are presented in Tables 2 and 5, e.g., peptides consisting of SEQ ID NO:7, 8, 9, 10, 11, 12, 13, 14, or 15, or P3V10, P3V11, or P3V24.

In a related aspect, the present invention provides a composition comprising the P3 variant polypeptide described above and herein along with a physiologically acceptable excipient. In some embodiments, the P3 variant polypeptide consists of SEQ ID NO:1 with N-terminal acetylation and C-terminal amidation, optionally with further N-terminal lipidation by N-acylation with palmitic acid. In some embodiments, the P3 variant may be one shown in Tables 2 and 5, e.g., SEQ ID NO:7, 8, 9, 10, 11, 12, 13, 14, or 15, or P3V10, P3V11, or P3V24. In some embodiments, the polypeptide further comprises another therapeutic agent effective for treating a polyQ disease, e.g., a polyQ protein toxicity inhibitor such as P42 or QBP1.

In a second aspect, the present invention provides a method for treating a polyQ disease in a subject. The method includes the step of administering to the subject an effective amount of a P3 variant polypeptide described above and herein. In some embodiments, the P3 variant polypeptide consists of SEQ ID NO:1 with N-terminal acetylation and C-terminal amidation, optionally further comprising N-terminal lipidation by N-acylation with palmitic acid. In other embodiments, the P3 variant may be one shown in Tables 2 and 5, e.g., SEQ ID NO:7, 8, 9, 10, 11, 12, 13, 14, or 15, or P3V10, P3V11, or P3V24. In some embodiments, another therapeutic agent effective for treating a polyQ disease is co-administered to the patient. In some embodiments, the P3 variant polypeptide is administered orally, intravenously, intramuscularly, intraperitoneally, or subcutaneously. The polypeptide may be administered once daily, weekly, or monthly. Typically, about 1-10,000 mg, about 10-1,000 mg, about 10-100 mg, about 20-50 mg, or about 10, 20, 30, 40, or 50 mg of the polypeptide is administered each time to the subject per kg of the subject's body weight. The subject to receive such treatment is one who has been diagnosed with a polyQ disease or is at risk of developing a polyQ disease.

In a related aspect, the present invention indicates the use of a P3 variant peptide in the manufacture of a medicament for treating a polyQ disease in a subject. As described herein, this P3 variant polypeptide is derived from the wild-type P3 sequence of SEQ ID NO:1. For example, the P3 variant polypeptide P3V8 consists of SEQ ID NO:1 with N-terminal acetylation and C-terminal amidation, optionally further comprising N-terminal lipidation by N-acylation with palmitic acid. In some cases, the medicament is formulated for specific means of administration to patients, for example, for oral administration or for injection such as for intravenous, intramuscular, intraperitoneal, or subcutaneous injection. In some cases, the medicament further comprises another therapeutic agent effective for treating a polyQ disease. In some cases, the medicament is formulated in a dose form containing an effective amount of the polypeptide for one administration.

In a third aspect, the present invention provides a kit for treating a polyQ disease. The kit comprises a container containing a pharmaceutical composition comprising a P3 variant polypeptide described herein (e.g., P3V8 or lipidated P3V8), which is capable of inhibiting expanded CAG-RNA mediated toxicity as verified in an in vitro or in vivo assay. In some embodiments, the kit further comprises a second container containing a second therapeutic agent known to be effective for treating a polyQ disease, such as polyQ protein toxicity inhibitor P42 or QBP1. In some embodiments, the kit further comprises informational material providing instructions on administration of the pharmaceutical composition.

BRIEF DESCRIPTION OF THE DRAWINGS

(FIG. 1A) Effect of P3WT on suppressing DsRed$_{CAG100}$ neurodegeneration in *Drosophila*. (FIG. 1B) Statistical analysis of panel (FIG. 1A). (FIG. 1C) Effect of P3V5 on suppressing DsRed$_{CAG100}$ neurodegeneration in *Drosophila*. (FIG. 1D) Statistical analysis of panel (FIG. 1C). (FIG. 1E) Effect of P3V8 on suppressing DsRed$_{CAG100}$ neurodegeneration in *Drosophila*. (FIG. 1F) Statistical analysis of panel (FIG. 1E). Pseudopupil assay was performed on 12 day-old adult flies. The flies were of genotypes w; gmr-GAL4 UAS-DsRed$_{CAG0}$/+; +/+ and w; gmr-GAL4/+; UAS-DsRed$_{CAG100}$/+. Data are expressed as mean±S.E.M. for at least 3 independent experiments. *Indicates P<0.05, indicates P<0.01 and *indicates P<0.001.

(FIG. 3A) Dose-dependent effect of synthetic P3WT in the absence or presence of DeliverX on the inhibition of cell death in EGFP$_{CAG78}$ RNA-expressing HEK293 cells. (FIG. 3B) Dose-dependent effect of synthetic P3V8 in the absence or presence of DeliverX on the inhibition of cell death in EGFP$_{CAG78}$ RNA-expressing HEK293 cells. Left of the charts: various amount of P3WT (FIG. 3A) or P3V8 (FIG. 3B) were transfected into individual culture wells by DeliverX 4 hr after plasmid transfection. Right of the charts: P3WT (FIG. 3A) or P3V8 (FIG. 3B) was added into individual culture wells immediately after plasmid transfection. A lactate dehydrogenase (LDH) cytotoxicity assay was performed. (FIG. 3C) Treatment of P3V8 (with DeliverX) restored pre-45s rRNA levels in EGFP$_{CAG78}$ RNA-expressing HEK293 cells. Cells were transfected with various amount of P3V8 using DeliverX. Data are presented as fold change of the relative pre-45s rRNA expression levels compared with the untransfected samples. Experiments were repeated at least 3 times and data are expressed as mean±S.E.M. NS indicates no significance. *Indicates P<0.05, indicates P<0.01, *indicates P<0.001 and ****indicates P<0.0001.

(FIG. 4A) Chemical structure of L1P3V8. (FIG. 4B) Comparison of cellular uptake level of P3V8 and L1P3V8 in HEK293 cells. Cellular uptake level was measured 3 hr after 100, 500 or 1000 nM treatment of respective peptide. The total amount of peptide in the cell lysate was normalized to total protein level in cell lysate. (FIG. 4C) Dose-dependent effect of synthetic L1P3V8 on the inhibition of cell death in EGFP$_{CAG78}$ RNA-expressing HEK293 cells. Various amount of L1P3V8 were added into individual culture wells immediately after plasmid transfection. LDH cytotoxicity assay was performed. The IC$_{50}$ value represents the concentration of peptides that reduced LDH enzyme activity by 50% when compared with the no peptide treatment control group. (FIG. 4C) Effect of L1P3V8 on suppressing DsRed-CAG$_{100}$ neurodegeneration in *Drosophila*. (FIG. 4D) Statistical analysis of panel (FIG. 4C). Pseudopupil assay was performed on 12 day-old adult flies. The flies were of genotypes w; gmr-GAL4 UAS-DsRed$_{CAG0}$/+; +/+ and w; gmr-GAL4/+; UAS-DsRed$_{CAG100}$/+. Data are expressed as mean±S.E.M. for at least 3 independent experiments. *Indicates P<0.05 and **indicates P<0.01.

(FIG. 5A) Inhibitor plasma concentration-time profiles of P3V8 and L1P3V8 following intravenous administration. (FIG. 5B) Brain concentrations of P3V8 (n.d.: not detected) and L1P3V8 at 20 min after intravenous administration (FIG. 5C) Inhibitor plasma concentration-time profiles of inhibitors administered via the intranasal route after pre-treatment with 0.5% chitosan. (FIG. 5D) Brain concentrations of P3V8 and L1P3V8 at 20 min after intranasal administration. Data are presented as mean±S.E.M. for 6 independent experiments. **Indicates P<0.01.

DEFINITIONS

Figure 1A:
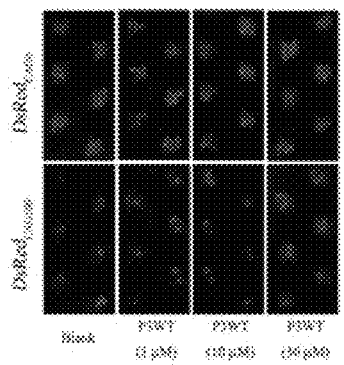
FIGS. 1A-1F P3V8 most effectively suppresses expanded CAG RNA-induced RNA toxicity in vivo.
Figure 1B:
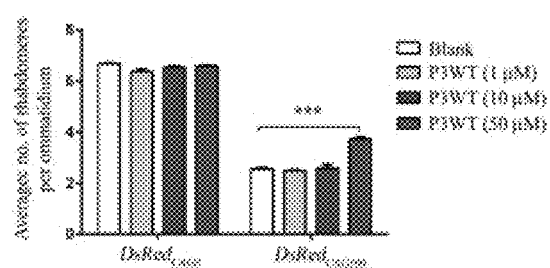
Figure 1C:
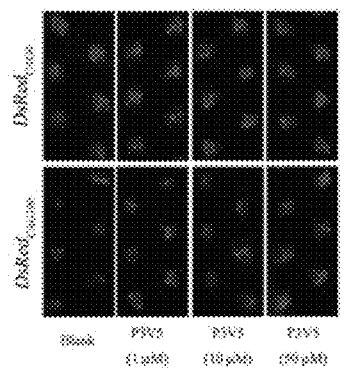

The term "inhibiting" or "inhibition," as used herein, refers to any detectable negative effect on a target biological process, such as expanded CAG-RNA mediated or PolyQ-mediated toxicity. Typically, an inhibition of expanded CAG-RNA mediated or PolyQ-mediated toxicity is reflected in a decrease of at least 10%, 20%, 30%, 40%, 50%, 60%, 70%, 80%, 90% or higher, including 100% or complete elimination, of one or more hallmarks of expanded CAG-RNA mediated or PolyQ-mediated toxicity as described herein, when compared to a control not given the "inhibition" treatment, such as treatment by administration of small molecule therapeutics described herein. On the other hand, inhibition of expanded CAG-RNA mediated or PolyQ-mediated toxicity may also be manifested as increased cell survival, demonstrated in an increase of at least 50%, 60%, 70%, 80%, 90%, 100%, 200%, 300%, 500% or more in the number or length of time of cell survival in the pertinent tissues within the recipient body after the small molecule administration in comparison to a control that has not received the same treatment.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a core amino acid sequence responsible for expanded CAG-RNA binding has at least 80% identity, preferably 85%, 90%, 91%, 92%, 93, 94%, 95%, 96%, 97%, 98%, 99%, or 100% identity, to a reference sequence, e.g., SEQ ID NO:1), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the term "treatment" or "treating" includes both therapeutic and preventative measures taken to address the presence of a disease or condition or the risk of developing such disease or condition at a later time. It encompasses therapeutic or preventive measures for alleviating ongoing symptoms, inhibiting or slowing disease progression, delaying of onset of symptoms, or eliminating or reducing side-effects caused by such disease or condition. A preventive measure in this context and its variations do not require 100% elimination of the occurrence of an event; rather, they refer to an inhibition or reduction in the likelihood or severity of such occurrence or a delay in such occurrence.

A "polyQ disease," as used herein, refers to a disease or condition that is associated with, caused by, or exacerbated by, RNA containing an expanded long repeats of CAG trinucleotides (expanded CAG-RNA) and/or polyQ polypeptides, which may be encoded by the expanded CAG-RNA. PolyQ diseases include those diseases, conditions, and symptoms that result from nucleolar stress or endoplasmic reticulum stress caused by expanded CAG-RNA, polyQ polypeptides, or both. As such, the presence of a polyQ disease can be observed at a cellular level by detecting or measuring one or more of the hallmarks of expanded CAG-RNA mediated cytotoxicity or polyQ-mediated cytotoxicity. Additionally, the presence of a polyQ disease can be indicated by the presence of expanded CAG-RNA or polyQ polypeptides in pertinent cells/tissues of a person being tested for the disease. Furthermore, cells or tissues taken from or present in the body of a patient suffering from polyQ disease or suspected to suffer from a polyQ disease, e.g., due to hereditary patterns, can exhibit one or more of the hallmarks of expanded CAG-RNA mediated cytotoxicity or polyQ-mediated cytotoxicity to indicate the presence of a polyQ disease, regardless of whether clinical symptoms of the polyQ disease are apparent at the time. Exemplary polyQ diseases include Huntington's Disease (HD), Dentatorubropallidoluysian atrophy (DRPLA), Spinocerebellar ataxia (SCA) Type 1, Spinocerebellar ataxia Type 2, Machado-Joseph Disease (MJD/SCA3), Spinocerebellar ataxia Type 6, Spinocerebellar ataxia Type 7, Spinocerebellar ataxia Type 17, and Spinal and bulbar muscular atrophy, X-linked 1 (SMAX1/SBMA).

The term "effective amount," as used herein, refers to an amount that produces therapeutic effects for which a substance is administered. The effects include the prevention, correction, or inhibition of progression of the symptoms of a disease/condition and related complications to any detectable extent, e.g., one or more of the hallmarks of expanded CAG-RNA mediated cytotoxicity or polyQ-mediated cytotoxicity. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" when used in reference to a given value denotes a range encompassing ±10% of the value.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

"Translocation sequence" or "transduction sequence" refers to a peptide or protein (or active fragment or domain thereof) sequence that directs the movement of a protein from one cellular compartment to another, or from the extracellular space through the cell or plasma membrane into the cell. Examples include the TAT transduction domain (see, e.g., S. Schwarze et al., *Science* 285 (Sep. 3, 1999); penetratins or penetratin peptides (D. Derossi et al., *Trends in Cell Biol.* 8, 84-87); and Herpes simplex virus type 1 VP22 (A. Phelan et al., *Nature Biotech.* 16, 440-443 (1998). Translocation peptides can be fused (e.g. at the amino and/or carboxy terminus), conjugated, or coupled to a polypeptide of the present invention, in order to produce a conjugate compound such as a fusion peptide that may pass into target cells, or through the blood brain barrier and into target cells more easily.

As used herein, the term "nucleolin" or "NCL" refers to the nucleolin protein. Exemplary nucleolin proteins include those of the Chinese Hamster (Genbank Accession No. AAA36966.1), the golden hamster (Genbank Accession No. P08199.2), the Norwegian Rat (Genbank Accession No. EDL75577.1), the house mouse (Genbank Accession No. EDL40222.1), and human nucleolin (Genbank Accession No. EAW70962.1). Nucleolin contains three RNA recognition motif (RRM) domains, RRM1, RRM2, and RRM3. It has been reported that certain peptides derived from NCL are useful for treatment of expanded CAG-RNA mediated cytotoxicity or polyQ disease, for example, a P3 fragment derived from RRM2 and having the amino acid sequence of SEQ ID NO:1.

As used herein, the terms "P3 variant," "P3 variant peptide," and "P3 variant polypeptide" are used interchangeably to refer to a polypeptide that is generated from a core amino acid sequence SEQ ID NO:1 (a fragment derived from an RNA recognition motif of nucleolin (NCL) and previously known as P3, see, e.g., U.S. Patent Application Publication No. 2014/0357578 and in U.S. patent application Ser. No. 15/046,249) and contains one or more modifications made to SEQ ID NO:1 at one or more amino acid residues. The modifications may be deletion, addition, or substitution of the amino acid residue(s), for example substitution with naturally occurring amino acids or non-natural amino acids such as D-amino acids, or substitution of amino acids with peptide nucleic acid oligomers (PNA), as well as chemical modification of the N-terminus, C-terminus, or any side chain of one or more of amino acid residues within SEQ ID NO:1, such as acetylation, amidation, lipidation.

While the core amino acid sequence SEQ ID NO:1 may contain some variations such as amino acid deletion, addition, or substitution, it should maintain a substantial level sequence homology (e.g., at least 80%, 85%, 90%, 95%, 98%, or higher sequence homology) to SEQ ID NO:1. For example, residues 3, 5, 9, 12, and 13 of SEQ ID NO:1 remain unmodified in some embodiments, whereas other residues may be replaced with other natural (but different) amino acids or non-natural amino acids (such as D-amino acids). In other embodiments, the N- or C-terminus of the core sequence may be chemically modified, either directly or after initial modification, by means such as acetylation, amidation, lipidation, or glycosylation including PEGylation. Similarly, any of the side chains of amino acid residues of SEQ ID NO:1 may be chemically modified to generate P3 variants of desirable properties.

In any event, P3 variants are capable of binding RNA containing 1, 2, 3, 4, 5, 10, 15, 20, 25, 30, 35, 40, 50, 60, 75, 78, 100, or more CAG triplet nucleotide repeats with higher affinity that the original P3 peptide of SEQ ID NO:1, preferably with about twice or higher affinity, for example, about 5 times, about 10 times, about 20 times, about 25 times, or even about 50 times higher in comparison the unmodified P3 peptide. In addition to this modified core sequence that is responsible for the polypeptide's ability to bind to expanded CAG-RNA, one or more amino acid sequences of a homologous origin (e.g., additional sequence derived from the same protein, NCL) or a heterologous origin (e.g., an amino acid sequence derived from another unrelated protein) can be included in the P3 variant polypeptide at the N- and/or C-terminus. In this disclosure, the P3 variant peptides are typically shorter than full length NCL and definitely different from any natural fragment of NCL. For example, such peptides can be shorter in length, e.g., less than 714 amino acids in length or less than about 20, 25, 30, 50, 75, 100, 150, 200, 250, 300, 350, 400, 500, 600, or 700 amino acids in length. Some examples of such P3 variants are provided in Tables 2 and 5.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) Nature 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

As used herein, the terms "$(CAG)_n$-mediated toxicity," "expanded CAG-RNA mediated cytotoxicity," and the like refer to cytotoxicity caused by expanded CAG-RNA. Expanded CAG-RNA mediated toxicity can result in nucleolar stress and cell death. Expanded CAG-RNA mediated toxicity can be inferred by detecting or measuring one or more of (i) rRNA upstream control element hypermethylation, (ii) a decrease in rRNA transcription, (iii) a decrease in binding of NCL to the rRNA locus, (iv) an increase in binding between ribosomal proteins and MDM2, (v) stabilization of p53, (vi) accumulation of p53 in the mitochondria, (vii) release of Bcl-xL from Bak, (viii) release of cytochrome c from the mitochondria, (ix) caspase activation, and (x) apoptosis or cell death.

As used herein, the terms "PolyQ-mediated cytotoxicity," "PolyQ-mediated toxicity," and the like refer to cytotoxicity caused by polypeptides that contain polyglutamine amino acid sequences. PolyQ-mediated cytotoxicity can result in cellular stress, endoplasmic reticulum stress, an unfolded protein response, and cell death. PolyQ-mediated cytotoxicity can be inferred by detecting or measuring one or more of (i) GRP78/BiP upregulation, (ii) caspase activation, and (iii) apoptosis or cell death. PolyQ-mediated cytotoxicity can be observed independently of expanded CAG-RNA mediated cytotoxicity by measuring GRP78/BiP upregulation as explained herein. Similarly, expanded CAG-RNA mediated cytotoxicity can be observed independently of polyQ-mediated cytotoxicity by measuring one or more of rRNA hypermethylation, NCL binding to rRNA locus, the level of rRNA expression, and binding between ribosomal proteins and MDM2 as explained herein.

RNA that contains CAG triplet nucleotide repeats can cause expanded CAG-RNA mediated cytotoxicity and polyQ-mediated cytotoxicity when the CAG repeats are translated. In some cases, the CAG repeats are not in a translated region and the expanded CAG-RNA can cause expanded CAG-RNA mediated cytotoxicity but not polyQ-mediated cytotoxicity. Similarly, if a polyglutamine polypeptide is encoded by an mRNA that does not contain CAG triplet nucleotide repeats, it can cause polyQ-mediated cytotoxicity but not expanded CAG-RNA mediated cytotoxicity.

For example, a polyglutamine polypeptide can be encoded by CAG/A repeats (alternating CAG and CAA, which both encode glutamine), CAA/G repeats (alternating CAA and CAG), CAA repeats, or a combination thereof. Cells that contain expanded CAG-RNA or polyQ polypeptides can be detected by detecting expanded CAG-RNA or polyQ peptide directly, or by detecting or measuring any of the hallmarks of expanded CAG-RNA toxicity or polyQ peptide toxicity.

The term "consisting essentially of," when used in the context of describing a composition containing an active ingredient, refer to the fact that the composition does not contain other ingredients possessing any similar or relevant biological activity. For example, a composition consisting essentially of an inhibitor of expanded CAG-RNA mediated or PolyQ-mediated toxicity is a compound that does not contain other modulators such as enhancers or inhibitors of expanded CAG-RNA mediated or PolyQ-mediated toxicity.

DETAILED DESCRIPTION OF THE INVENTION

I. Introduction

Polyglutamine (polyQ) diseases are a group of late-onset, dominant genetic disorders characterized by expanded CAG repeats in the coding region of the associated genes, which are translated into expanded polyQ domains in disease proteins. Recent findings demonstrate that the CAG-repeat RNA plays a crucial role in polyQ pathogenesis. The inventors' research group have previously identified a peptic fragment, termed P3 (amino acid sequence Asp-Gly-Lys-Ser-Lys-Gly-Ile-Ala-Tyr-Ile-Glu-Phe-Lys, SEQ ID NO:1), which was derived from the human nucleolin protein and demonstrated suppression activity of the CAG RNA-induced nucleolar stress pathway, cell death, and neurodegeneration in both in vitro and in vivo disease models. In this study, the inventors have generated and tested a series P3 variant peptide inhibitors, P3Vs, which were designed based on the P3 prototype sequence and then subsequently modified. Some of these variants have shown desirable characteristics that are indicative of therapeutic effectiveness. For example, one P3 variant interacts directly with the CAG-repeat RNA more strongly (about 25-fold) than P3. Another modification has enabled P3 to achieve brain uptake in rats. It has been further discovered that terminal modifications of the P3 peptide largely improves the potency of the peptide inhibitor by about 200 fold. In summary, in this latest study a series of good lead peptide inhibitors were developed for targeting polyQ diseases, and their ability for brain uptake and enhanced bioactivities have been demonstrated both in vitro and vivo.

The inventors have previously demonstrated that the expanded CAG RNA triggers nucleolar stress and eventually induces toxicity in polyglutamine diseases. In early 2016, they reported a 13-amino acid sequence (P3) within the RRM2 domain of the nucleolin protein that can physically interacts with expanded CAG RNA and suppress toxicity both in vitro and in vivo disease models. The inventors then rationally modified the P3 sequence and generated a series of P3 variant peptide inhibitors (P3Vs). It was then explored whether modifications at the N- and C-termini could improve the binding and inhibitory activity of P3. N-terminal acetylation and C-terminal amidation neutralize the charges at both end of the peptide and may increase its biological activity. The KD value of P3V9 was determined to be 2 µM using isothermal titration calorimetry, indicating that C-terminal amidation improved the peptide affinity to expanded RNA. When the N-terminus was also acetylated, the dissociation constant of P3V8 was further lowered to 0.33 µM.

Acylation of peptides with long-chain lipids has been shown to improve their in vivo half-life, membrane permeability, and change their pharmacokinetic property. Importantly, lipid solubility is key factor for the transportation of inhibitors across the blood-brain barrier. To test if lipidation could improve the in vivo stability of P3V8, the peptide was N-terminally lipidated by N-acylation with palmitic acid to provide L1P3V8. The in vivo stability of P3V8 was then compared with L1P3V8. The results demonstrated that, when compared to apo-P3V8, the stability of the lipidated P3V8 (L1P3V8) significantly improved in both rat plasma and rat brain homogenates at 37° C. At the concentration of 2000 ng/mL, only 20.7% and 3.3% of P3V8 was remained in plasma and brain homogenates respectively after 1-hour incubation. In contrast, around 98.8% and 45.0% of L1P3V8 remained intact after 1-hour incubation and around 86.9% and 21.2% were stable after 3-hour incubation in plasma and brain homogenate, respectively. The results demonstrated that lipidation of P3V8 significantly improved its stability in both plasma and the brain.

Further, P3 variants retain the ability to effectively rescue polyQ cytotoxicity and neurodegeneration in in vitro and in vivo models, respectively. The P3Vs are therefore good lead inhibitors for the next level of pharmaceutical development.

II. Compositions

A. Inhibitors of $(CAG)_n$-Mediated Toxicity

In some embodiments, compositions are provided that reduce $(CAG)_n$-mediated toxicity in a cell. Reduction of $(CAG)_n$-mediated toxicity can, in some cases, restore rRNA transcription in expanded CAG RNA-expressing cells. For example, synthetic peptides are provided that can bind to or sequester toxic RNA species. In some cases, the synthetic peptides are fragments derived from full-length nucleolin (NCL) and then modified by a variety of possible means but do not encompass the full-length NCL. For example, the synthetic peptides may be derived from an RNA recognition motif (RRM) of full-length nucleolin, especially from the RRM2 domain of NCL, such as the P3 fragment, which is then subject to additional modification to one or more amino acid residues. The peptides optionally may include one or more additional amino acid sequences from a heterologous origin, i.e., a source other than the NCL protein.

In some cases, compositions for treating $(CAG)_n$-mediated RNA toxicity in a cell include one or more of the above synthetic peptides. For example, compositions for treating $(CAG)_n$-mediated RNA toxicity in a cell can include peptide P3 and/or P3L as well as those described in U.S. Patent Application Publication No. 2014/0357578 and in U.S. patent application Ser. No. 15/046,249.

In some cases, the peptides are conservatively substituted at one or more of the amino acid residues of SEQ ID NO:1. The residues of peptides can also be substituted with natural (but different) or non-natural amino acids, such as D-amino acids or chemically modified natural amino acids. In some cases, the peptides are truncated. Truncated peptides include peptides in which one or more (e.g., two) amino or carboxy terminal residues are removed and optionally replaced with analogous substituents such as PNA or the like. In some cases, the peptides are internally deleted such that one or more amino acids that are not at the amino or carboxy terminus are removed. In some cases, the peptides can be modified by the addition of one or more amino acids at the amino or carboxy terminus. For example, a linker or purification tag can be fused to the amino or carboxy terminus. Alternatively, the peptides can be inserted into a scaffold region of a protein, polypeptide, or other molecule as described herein. A scaffold may provide enhanced stability of the peptide in the cell, and may improve binding by reducing the conformational freedom of the peptide or influencing its three-dimensional structure.

For example, one or more of the peptides can be inserted into the CDR region of an antibody scaffold. Alternatively, non-immunoglobulin protein scaffolds can be used as peptide frameworks. See, e.g., Ku et al. (*Proc. Natl. Acad. Sci. U.S.A.* 92 (14):6552-6556 (1995)) disclosing the use of cytochrome b562 as a scaffold; U.S. Pat. Nos. 6,818,418 and 7,115,396 disclosing the use of a fibronectin or fibronectin-like protein scaffolds; Beste et al. (*Proc. Natl. Acad. Sci. U.S.A.* 96 (5):1898-1903 (1999)) disclosing a lipocalin-based scaffold; U.S. Pat. No. 5,770,380 disclosing a synthetic rigid, non-peptide organic scaffold of calixarene, attached with one or more multiple variable peptide loops used as binding sites; and Murali et al. (*Cell Mol Biol* 49 (2):209-216 (2003)) describing a methodology for reducing antibodies into smaller peptidomimetics, termed "antibody like binding peptidomimetics" (ABiP) which may also be useful as a protein scaffold.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody scaffolds can also include such compounds.

B. Production of Peptides that Inhibit $(CAG)_n$-Mediated RNA Toxicity i. General Recombinant Technology Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a nucleolin gene, a polynucleotide encoding a polypeptide comprising the expanded CAG-RNA binding domain RRM2 or a peptide derived therefrom, and synthetic oligonucleotides can be verified after cloning or subcloning, e.g., the chain termination method for sequencing double-stranded templates of Wallace et al., *Gene* 16: 21-26 (1981).

ii. Coding Sequence for a P3 Variant Polypeptide

Polynucleotide sequences encoding nucleolin or its RRM domains have been determined and may be obtained from a commercial supplier or recombinantly produced.

Upon acquiring a nucleic acid sequence encoding a P3 variant peptide that binds expanded CAG-RNA with higher affinity in comparison to P3, the coding sequence can be further modified by a number of well-known techniques such as restriction endonuclease digestion, PCR, and PCR-related methods to generate coding sequences for the P3 variant polypeptide. The polynucleotide sequence encoding a desired P3 variant polypeptide can then be subcloned into a vector, for instance, an expression vector, so that a recombinant polypeptide can be produced from the resulting construct. Further modifications to the coding sequence, e.g., nucleotide substitutions, may be subsequently made to alter the characteristics of the polypeptide.

A variety of mutation-generating protocols are established and described in the art, and can be readily used to modify a polynucleotide sequence encoding a P3 variant polypeptide. See, e.g., Zhang et al., *Proc. Natl. Acad. Sci. USA*, 94: 4504-4509 (1997); and Stemmer, *Nature*, 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science*, 229: 1193-1201 (1985)), mutagenesis using uracil-containing templates (Kunkel, *Proc. Natl. Acad. Sci. USA*, 82: 488-492 (1985)), oligonucleotide-directed mutagenesis (Zoller and Smith, *Nucl. Acids Res.*, 10: 6487-6500 (1982)), phosphorothioate-modified DNA mutagenesis (Taylor et al., *Nucl. Acids Res.*, 13: 8749-8764 and 8765-8787 (1985)), and mutagenesis using gapped duplex DNA (Kramer et al., *Nucl. Acids Res.*, 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

iii. Modification of Nucleic Acids for Preferred Codon Usage in a Host Organism

The polynucleotide sequence encoding a P3 variant polypeptide can be further altered to coincide with the preferred codon usage of a particular host. For example, the preferred codon usage of one strain of bacterial cells can be used to derive a polynucleotide that encodes a recombinant polypeptide of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the P3 variant polypeptides.

iv. Chemical Synthesis of a P3 Variant Polypeptide

A P3 variant polypeptide can also be chemically synthesized using conventional peptide synthesis or other protocols well known in the art.

While proteins generally are prepared by recombinant methods, chemical synthesis is the prevailing method the preparation of peptides. This is due to the ease, predictability, and flexibility of chemical synthesis, which also allows the convenient incorporation of many non-proteinogenic modifications. Peptide synthesis has allowed the preparation of numerous peptides, from laboratory scale up to ton-scale. The methods in solid-phase peptide synthesis (SPPS) are defined by the set of $N^\alpha$-protecting groups, side-chain protecting groups, coupling reagents, linkers (handles), as well as the solid supports which can be used (Peptide Synthesis and Applications, Knud J. Jensen, A. Pernille Tofteng, Soren L. Pedersen (Eds), Springer Protocols, Humana Press, 2013.).

The two most generally used protecting groups in SPPS are the fluoren-9-ylmethyloxycarbonyl (Fmoc) ((a) Carpino L. A. and G. Y. Han (1970) The 9-Fluorenylmethoxycarbonyl function, a new base-sensitive amino-protecting group. *J. Am. Chem. Soc.*, 92, 5748-5749, (b) Carpino L. A. and G. Y. Han (1972) The 9-fluorenylmethoxycarbonyl function amino-protecting group. *J. Org. Chem.* 37, 3404-3409.) and the tert-butoxycarbonyl (Boc), with each $N^\alpha$-protecting group defining an overall strategy for SPPS. The chemical conditions for removal of these transient protecting groups, i.e. base vs. acid, each define a 'chemical window' of opportunities for the other chemical steps in the overall SPPS strategy. Therefore the solid-phase strategy is defined by the choice of the $N^\alpha$-protecting group for the amino acid building blocks. The Fmoc group can be removed under mild conditions with secondary amines, typically a 1:4 solution of piperidine in DMF ((a) Atherton E., H. Fox, D. Harkiss, C. J. Logan, R. C. Sheppard and B. J. Williams (1978) Mild procedure for solid-phase peptide synthesis—Use of the fluorenylmethoxycarbonyl amino acids. *Chem. Commun.* 537-539, (b) Atherton E., H. Fox, Harkiss, D. and Sheppard, R. C. (1978) Application of polyamide resins to polypeptide synthesis—Improved synthesis of betal-endorphin using fluorenylmethoxycarbonyl amino acids. *Chem. Commun.* 539-540.). For some trifunctional amino acids such as Cys, Asp, Glu, Lys, side-chain protection is essential for successful peptide synthesis, however, generally all other tri-functional amino acids are also semi-permanently side-chain protected. The currently used protecting groups are tert-butyl (t-Bu) ester for Glu and Asp; t-Bu ether for Ser, Thr, and Tyr; 2,2,4,6,7-pentamethyl-dihydrobenzofuran-5-sulfonyl (Pbf) for Arg; and trityl (Trt) for Cys, Asn, Gln, and His.

Activation of the carboxylic acid moiety of the amino acid is required to be able to react with the $N^\alpha$-amino group of the growing peptide chain. The first step is the reaction with an electrophile, in some cases in the presence of a base. Carbodiimide based coupling reagents, such as DCC or DIC (N,N'-diisopropylcarbodiimide; FIG. 1), have been used for decades (FIG. 1, 5). A potential side-reaction with carbodiimide-based reagents is the O-to-N rearrangement of the O-acylisourea intermediate and 'overactivation' by formation of the symmetrical anhydride, which can lead to epimerization. These side-reactions can be prevented by the addition of an auxiliary nucleophiles such as 1-hydroxybenzotriazole (HOBt) (König W. and Geiger, R. (1970) Eine neue Methode zur Synthese von Peptiden: Aktivierung der Carboxylgruppe mit Dicyclohexylcarbodiimid unter Zusatz von 1-Hydroxy-benzotriazolen. *Chem. Ber.-Recl.* 103, 788-798), or 1-hydroxy-7-azabenzotriazole (HOAt) (Carpino, L. A. (1993) 1-Hydroxy-7-azabenzotriazole. An efficient peptide coupling additive, *J. Am. Chem. Soc.*, 115, 4397-4398), which form the corresponding activated esters. A relative newcomer is ethyl 2-cyano-2-(hydroxyimino)acetate (Oxyma) (Subirós-Funosas R., Prohens, R., Barbas, R., El-Faham, A. and Albericio, F. (2009) Oxyma: An Efficient Additive for Peptide Synthesis to Replace the Benzotriazole-Based HOBt and HOAt with a Lower Risk of Explosion. *Chem. Eur. J.* 15, 9394-9403). Auxiliary nucleophiles, such as HOBt, ensure that the optical integrity of the stereogenic center at the C-terminal of the activated amino acid residue is maintained throughout the coupling step.

Numerous so-called in situ coupling reagents have been developed to reduce coupling time and minimize epimerization. The most important are HBTU (N-[(1H-benzotriazol-1-yl)(dimethylamino)methylene]-N-methylmethanaminium hexafluorophosphate N-oxide) (Dourtoglou V., Gross, B., Lambropoulou, V. and Zioudrou, C. (1984) O-Benzotriazolyl-N,N,N',N'-tetramethyluronium hexafluorophosphate as coupling reagent for the synthesis of peptides of biological interest, *Synthesis*, 572-574), HATU (N-[(dimethylamino)-1H-1,2,3-triazole[4,5-b]pyridine-1-ylmethylene]-N-methylmethanaminium hexafluorophosphate N-oxide), PyBOP (1-benzotriazolyloxy-tris-pyrrolidinophosphonium hexafluorophosphate) and the novel COMU (1-[(1-(Cyano-2-ethoxy-2-oxoethylideneaminooxy)-dimethylamino-morpholino-methylene)] methanaminium hexafluorophosphate) (El-Faham A., Funosas, R. S., Prohens, R. and Albericio, F. (2009) COMU: A safer and more effective replacement for benzotriazole-based uronium coupling reagents. *Chem. Eur. J.* 15, 9404-9416) reagents.

While polystyrene is an inexpensive resin that has been used widely, especially in Boc-SPPS and in Fmoc-SPPS of shorter sequences, other resins provide certain advantages. An important class of resins is constructed from a polystyrene core onto which PEG chains have been attached. TentaGel carries amino groups at the end of the PEG chains.

For the synthesis of peptides with a C-terminal carboxylic acid, 4-alkoxybenzyl alcohol type (Wang) linkers are an obvious choice. Other linkers for the synthesis of peptide acids include trityl based handles, e.g. chloro-trityl chloride linker developed by Barlos. For syntheses of peptides as their C-terminal amides in Fmoc-SPPS, the most common linker is a benzhydryl-type handle, the Rink amide linker, and the most commonly used resins are available with a Rink amide linker. The PAL ('Peptide Amide Linker') handle, which has a trisalkoxybenzyl structure is also very suitable for Fmoc-SPPS of peptide amides.

Suitably $N^\alpha$- and side-chain protected amino acids are coupled sequentially in the N←C direction to a growing peptide chain anchored to the resin. Typically, the C-terminal amino acid is first anchored at the carboxy terminus to the solid support via a cleavable handle. Then the $N^\alpha$-protecting group can be removed without affecting the side-chain protecting groups, thus the polypeptide chain is prepared for the next coupling cycle. SPPS reactions are driven to completion by the use of soluble reagents in excess, which can be removed by filtration and washing. Following the completion of the desired sequence of amino acids, the peptide is released from the solid support, and simultaneously the semi-permanent side-chain protecting groups are typically removed concomitantly.

In the case of a P3 variant comprising N- and/or C-terminus modification, including peptide nucleic acid oligomer (PNA) attachment, amidation, acetylation, lipidation, glycosylation, and the like, the core peptide can be synthesized first and then undergo chemical modification of one or more steps by well-known methods in the art.

B. Expression and Purification of Peptides that Inhibit $(CAG)_n$-Mediated RNA Toxicity Following verification of the coding sequence, a P3 variant polypeptide of the present invention can be produced using routine techniques in the field of recombinant genetics, relying on the polynucleotide sequences encoding the polypeptide disclosed herein.

i. Expression Systems

To obtain high level expression of a nucleic acid encoding a P3 variant polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the P3 variant polypeptide in host cells. A typical expression cassette thus contains a promoter operably linked to the nucleic acid sequence encoding the P3 variant polypeptide and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A⁺, pMTO10/A⁺, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the P3 variant polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant polypeptide (e.g., a P3 variant polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

ii. Transfection Methods

Standard transfection methods are used to produce bacterial, mammalian, yeast, insect, or plant cell lines that express large quantities of a P3 variant polypeptide, which is then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the P3 variant polypeptide.

iii. Purification of Recombinantly Produced Polypeptides

Once the expression of a recombinant P3 variant polypeptide in transfected host cells is confirmed, e.g., via an immunoassay such as Western blotting assay, the host cells are then cultured in an appropriate scale for the purpose of purifying the recombinant polypeptide.

1. Purification of Recombinantly Produced Polypeptides from Bacteria

When the P3 variant polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Additional methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a P3 variant polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide of the present invention, e.g., a P3 variant polypeptide, is expressed in host cells in a soluble form, its purification can follow the standard protein purification procedure described below. This standard purification procedure is also suitable for purifying a P3 variant polypeptide obtained from chemical synthesis.

(a) Solubility Fractionation

Often as an initial step, and if the protein mixture is complex, an initial salt fractionation can separate many of the unwanted host cell proteins (or proteins derived from the cell culture media) from the recombinant protein of interest, e.g., a P3 variant polypeptide of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

(b) Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a P3 variant polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

(c) Column Chromatography

The proteins of interest (such as a P3 variant polypeptide of the present invention) can also be separated from other proteins on the basis of their size, net surface charge, hydrophobicity, or affinity for ligands. In addition, antibodies raised against a P3 variant peptide can be conjugated to column matrices so as to allow the P3 variant polypeptide to be immunopurified. All of these methods are well known in the art.

It will be apparent to one of skill that chromatographic techniques can be performed at any scale and using equipment from many different manufacturers (e.g., Pharmacia Biotech).

iv. Verification of Activity

Once a P3 variant polypeptide is chemically synthesized or recombinantly produced, such as one generally fitting the structural profile described herein, the polypeptide can be then tested to verify its ability to suppress or inhibit cytotoxicity induced by CAG-repeat RNA in an in vitro or in vivo assay, e.g., any one of those known in the pertinent research field or described herein. An effective polypeptide can then be used in a therapeutic scheme for treating a patient suffering from or at risk of developing a polyQ disease, such as a human patient who has been diagnosed with a polyQ disease or who has a family history of a polyQ disease. Use of an effective polypeptide also encompasses the use of the polypeptide for manufacturing a medicament or a kit that is to be used for treating a polyQ disease.

III. Methods

Provided herein are methods for treating polyQ disease in a cell that contains an RNA containing a $(CAG)_n$ triplet nucleotide repeat. Such methods include contacting the cell with an effective amount of a composition (e.g., a P3 variant peptide) that reduces expanded-CAG RNA-mediated cytotoxicity. Methods of contacting can be performed in vitro and in vivo. In some cases, the RNA containing the $(CAG)_n$ triplet nucleotide repeat contains at least 10, 20, 30, 40, 50, 60, 70, 78, or 100 CAG triplet nucleotides. Such a cell is likely to exhibit nucleolar stress. In some cases, the composition itself binds the RNA containing the $(CAG)_n$ triplet nucleotide repeat. Such binding activity can act to sequester the RNA containing a $(CAG)_n$ triplet nucleotide repeat from disrupting cellular processes. For example, the composition can sequester the RNA containing a $(CAG)_n$ triplet nucleotide repeat from binding to nucleolin. In some cases, the cell expresses a nucleic acid encoding $MJD_{CAGn}$, or $DsRed_{CAGn}$, wherein each n is independently selected from about 10, 20, 30, 40, 50, 60, 70, 78, and 100. In some cases, the cell is from, or in, a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

Methods for treating a polyQ disease also include contacting a cell that expresses a peptide containing a polyQ amino acid sequence include the steps of contacting the cell with an effective amount of a composition that reduces polyQ-mediated cytotoxicity. In some cases, the composition itself binds the peptide containing the polyQ sequence. Such binding activity can act to sequester the polyQ peptide from disrupting cellular processes. For example, the composition can sequester the polyQ peptide from forming intracellular aggregates. In some cases, the cell expresses a nucleic acid encoding $MJD_{CAGn}$, $MJD_{CAA/Gn}$, or $MJD_{CAG/}$ $An$, wherein each n is independently selected from about 10, 20, 30, 40, 50, 60, 70, 78, and 100. In some cases, the cell is from, or in, a subject suffering from Huntington's Disease, Dentatorubropallidoluysian atrophy, Spinobulbar muscular atrophy, Spinocerebellar ataxia Type 1, Spinocerebellar ataxia Type 2, Machado-Joseph Disease, Spinocerebellar ataxia Type 6, Spinocerebellar ataxia Type 7, or Spinocerebellar ataxia Type 17.

IV. Pharmaceutical Compositions and Administration

The present invention also provides pharmaceutical compositions or physiological compositions comprising an effective amount of one or more P3 variant polypeptides, optionally with an additional compound known for treating polyQ mediated cytotoxicity, such as the peptide QBP1 (S N W K W W P G I F D, SEQ ID NO:34), P42, and Congo red.

Use of the compositions can be in both prophylactic and therapeutic applications for the treatment and prevention of a polyQ disease. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, L. Jorgensen, H. M. Nielsen (Eds.) Delivery Technologies for Biopharmaceuticals, Wiley, 2009.

The pharmaceutical compositions of the present invention can be administered by various routes, e.g., oral, subcutaneous, transdermal, intramuscular, intravenous, intranasal, or intraperitoneal administration. The preferred routes of administering the pharmaceutical compositions are intravenous or intraperitoneal delivery to a patient in need thereof (e.g., a human patient who is diagnosed of or is at risk of developing a polyQ disease) at doses of about 10-100,000 mg, 100-10,000 mg, 50-5,000 mg, 100, 200, 250, or 500 mg of each of the P3 variant polypeptide for a 70 kg adult human per day or every other day. Some exemplary doses and administration frequencies include about 0.5, 1, 2, 3, 4, 5, 6, 7, 8, 9, 10, 20, 30, 40, 50, 60, 70, 80, 90, or 100 mg/kg patient body weight for each polypeptide in each administration. Typically one or more polypeptides are administered to the patient either on once per day or per two-day basis. If more than one is administered, they can be administered at the same time or at separate times while all within the same general time frame. The polypeptide therapeutics may be administered in a single pharmaceutical composition or they may be in multiple separate compositions. Similarly, these polypeptides may be administered at the same time, or they may be administered on different days but all in close proximity to each other's administration, e.g., one administered on day 1 and other or others administered on day 2, such that the combined effects of these small molecules being co-administered are obtained. The appropriate dose may be administered in a single daily/bi-daily (once every other day) dose or as divided doses presented at appropriate intervals, for example as two, three, four, or more subdoses per day, or one dose every two, three, four, or five days For preparing pharmaceutical compositions of this invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a P3 variant peptide. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient (e.g., a P3 variant peptide). Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active component of a P3 variant polypeptide with encapsulating material as a carrier providing a capsule in which the small molecule (with or without other carriers) is surrounded by the carrier, such that the carrier is thus in association with the small molecule or the active component. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a P3 variant peptide) or sterile solutions of the active component in solvents comprising water, buffered water, saline, PBS, ethanol, or propylene glycol are examples of liquid compositions suitable for parenteral administration including subcutaneous, intramuscular, intravenous, or intraperitoneal administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a P3 variant polypeptide) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between about 3 and about 11, more preferably from about 5 to about 9, and most preferably from about 7 to about 8.

The pharmaceutical compositions one or more P3 variant polypeptides can be administered to a patient who have received a diagnosis of a polyQ disease or is at risk of developing such a disease at a later time in an amount sufficient to prevent, eliminate, reverse, or at least partially slow or arrest the symptoms of polyQ disease such as any of the clinical symptoms of the cytotoxicity related to, caused by, or enhanced by expanded CAG-repeat RNA or polyQ polypeptide. An amount adequate to accomplish this goal is defined as a "therapeutically effective dose." Amounts effective for this use will depend on the (expected) severity of the condition, route of administration, frequency of administration, and the body weight and general physical state of the patient, but generally range from about 0.5 mg to about 1000 mg per kg patient body weight, about 1 or 2 mg/kg to about 500 mg/kg, about 5-500 mg/kg, about 10-100 mg/kg, about 20-50 mg/kg, e.g., about 10, 20, 25, 30, 40, 50, or 80, 100, 150, 200, or 300 mg/kg body weight for each peptide therapeutic agent in each administration.

Single or multiple administrations of the compositions can be carried out with dose levels and pattern being selected by the treating physician. In any event, the pharmaceutical formulations should provide a quantity of a P3 variant polypeptide sufficient to effectively inhibit the undesired symptoms in the patient relating to expanded CAG-repeat RNA or polyQ polypeptide mediated cytotoxicity. Typically, the administration lasts at least 1, 2, 3, 4, 6, 8, 10, or 12 weeks and for as long as needed such as 6 months, 1, 2, 3, 4, 5, or 10, 15, 20 years on a daily, twice a day, bi-daily (once every other day), or weekly schedule.

While other active ingredient are generally not necessary to be co-administered to a recipient with the polypeptide therapeutics such as P3 variants in order to treat a patient suffering from or at risk of polyQ disease, it is optional that one or more additional therapeutically effective compounds may be co-administered along with the polypeptide(s), either in the same pharmaceutical composition(s) with the polypeptide(s) or in a separate pharmaceutical composition. For description of other therapeutic ingredients, see, e.g., U.S. Patent Application Publication No. 2014/0357578; and U.S. patent application Ser. No. 15/046,249.

V. Kits

The invention also provides kits for treating a polyQ disease according to the method of the present invention. The kits typically include a first container that contains a pharmaceutical composition comprising a P3 variant that is therapeutically effective to ameliorate the symptoms of a polyQ disease, such as P3V8 and the likes possessing a similar biological activity (e.g., capable of inhibiting cytotoxicity induced by expanded CAG-repeat RNA), optionally with an additional container that contains a pharmaceutical composition comprising another therapeutically effective compound for ameliorating the symptoms of a polyQ disease, such as another, different polypeptide or polynucleotide therapeutic agent including those described in U.S. Patent Application Publication No. 2014/0357578; and U.S. patent application Ser. No. 15/046,249, or any one of the known polyQ protein toxicity inhibitors such as P42, QBP1, and Congo red. In some variations of the kits, a single container may contain a pharmaceutical composition comprising two or more of compounds effective for treating a polyQ disease such as P3 variants of this invention, those described in U.S. Patent Application Publication No. 2014/0357578, as well as inhibitors of toxicity induced by polyQ proteins. The kits may further include informational material providing instructions on how to dispense the pharmaceutical composition(s), including description of the type of patients who may be treated (e.g., human patients who have received a diagnosis of a polyQ disease or have been deemed as risk of developing a polyQ disease, e.g., due to a strong propensity indicated by family history), the schedule (e.g., dose and frequency) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Introduction

Polyglutamine (PolyQ) diseases, including Machado Joseph Disease (MJD), represent a group of dominantly inherited progressive neurodegenerative diseases[1]. These diseases are characterized by expanded CAG trinucleotide repeat within the coding region, being translated into a polyQ stretch-containing disease protein[1]. It is widely accepted that the polyQ diseases toxicity is ascribed to the misfolding and aggregation of disease proteins[2-4].

However, accumulating evidence demonstrate that the expanded CAG-repeat RNA is another leading toxic factor in polyQ pathogenesis[5-8]. Various expanded CAG RNA pathogenic pathways have recently been described, and they include the recruitment of muscleblind-like (MBNL) proteins to expanded CAG-repeat RNA foci[9,10], the generation of small CAG RNAs via Dicer cleavage[11,12], and the activation of nucleolar stress[13,14].

Previously, it was demonstrated that the expanded CAG RNA triggers nucleolar stress and eventually induces toxicity in vitro and in vivo[13,14]. Nucleolar stress is a cellular response to the failure in ribosome biogenesis and/or ribosome malfunction[15]. A reduction in ribosomal RNA (rRNA) transcription causes an imbalance in the intracellular levels of ribosomal RNAs and ribosomal proteins, which subsequently triggers ribosome assembly defect and eventually leads to nucleolar stress-induced apoptosis[16,17]. Previous investigation showed that expanded CAG RNA physically interacts with the nucleolin (NCL) protein[13], a multi-functional nucleolar protein that plays critical roles in precursor rRNA (pre-rRNA) transcription[18], processing[19] and pre-ribosome assembly[18,20]. This RNA-protein interaction lead to upstream control element (UCE) hypermethylation and down-regulation of rRNA transcription, which induces nucleolar stress[13]. Recently, the inventors developed a 13-amino acid peptide inhibitor, P3 (Asp-Gly-Lys-Ser-Lys-Gly-Ile-Ala-Tyr-Ile-Glu-Phe-Lys, SEQ ID NO:1), which could inhibit the NCL-expanded CAG RNA interaction and suppress RNA toxicity in polyQ diseases[21]. The P3 peptide was designed based on the structure of RRM2 domain of NCL[21] which contains the ribonucleoprotein domain-1 (RNP-1) motif[22]. It has been shown that P3 could directly and preferentially bind to expanded continuous CAG-repeat RNA in vitro[21]. This P3-CAG RNA interaction titrated endogenous NCL away from binding to the toxic RNA, and restored the NCL-UCE interaction and pre-45s rRNA transcription[21]. Treatment of P3 suppressed expanded CAG RNA-induced cell death in mammalian cell model and neurodegeneration in *Drosophila* disease model[21]. The calculated maximal inhibitory concentration ($IC_{50}$) of P3 in inhibiting cell death was 4.369±1.140 $\mu M$[21]. In this study, the inventors performed peptide engineering on P3 and identified several variants that are more potent peptidylic inhibitors for targeting RNA toxicity in polyQ diseases.

Results

Alanine Scanning of P3

P3 is derived from the primary structure of NCL[21]. A series of P3 analogues was previously synthesized, in which basic or aromatic residues were substituted with Ala and their binding to expanded CAG RNA was measured to identify the amino acid side chains involved in the interaction with expanded CAG RNA. The results showed that Lys3, Lys5, Tyr9, and Phe12 are indispensable and serve as the pharmacophores for RNA binding[21]. To further illustrate how the mutations affect the interaction between P3 and RNA, isothermal titration calorimetry (ITC) experiments were performed to characterize the interaction between each individual mutant (Table 4) and expanded CAG RNA. All ITC experiments were performed using high ratios of peptide-to-RNA concentrations to increase the experiment's sensitivity. The heat generated by peptide dilution was determined by titrating the peptides into buffer only and was then subtracted from the binding titration curves of the corresponding peptides. The determined equilibrium dissociation constant $K_D$ of P3 is ~8.4 $\mu M$ with both favorable enthalpy ($\Delta H=-4.5$ kcal/mol) and entropy ($T\Delta S=2.4$ kcal/mol), suggesting that the peptide-RNA interaction is energetically driven by both favorable enthalpic and entropic components.

On the other hand, the determined equilibrium dissociation constant $K_D$ of P3MT3 and P3MT4 revealed that the mutations of the aromatic residues reduced the binding affinity to 16 and 17 $\mu M$ respectively, whereas mutations of the lysines (P3MT1, P3MT2 and P3MT5) had a more dramatic effect and reduced the affinity by ~3-12 fold (Table 4). In particular, the $K_D$ of P3MT2 and P3MT5 were increased to 100 $\mu M$ and 51 $\mu M$ respectively, indicating that among all the identified pharmacophores, Lys5 and Lys13 are most critical for RNA binding.

Amino Acid Substitutions of P3

Figure 6:
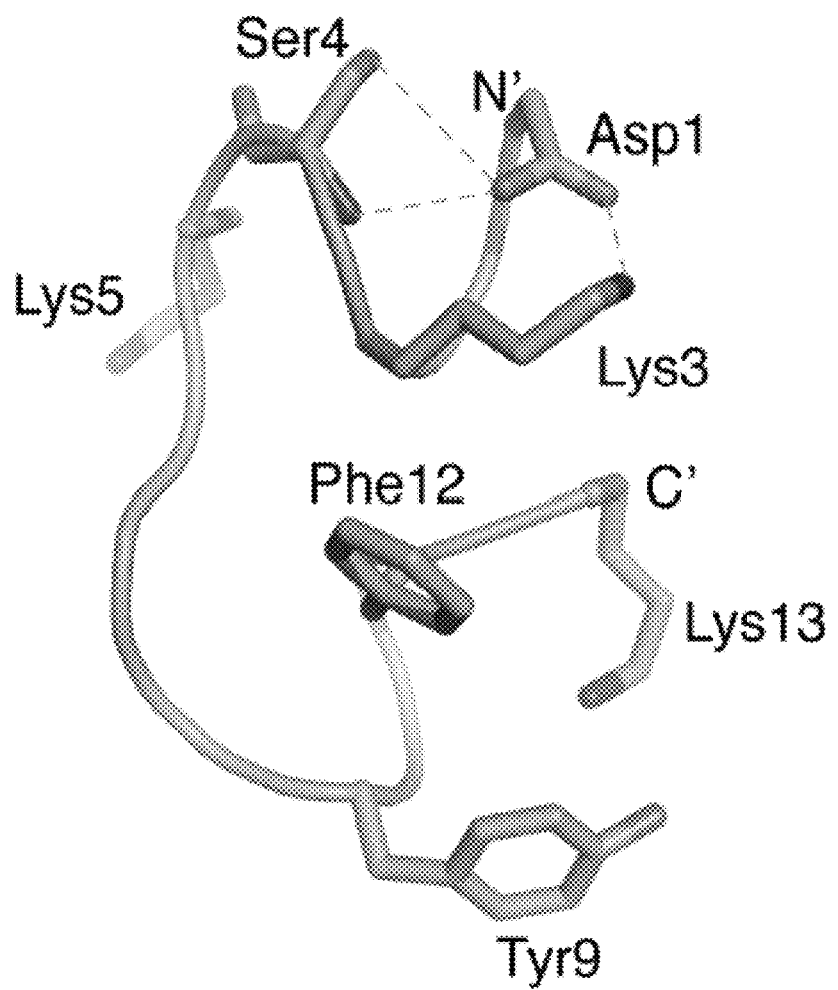
FIG. 6 Predicted fold of P3V8 peptide. 3D structure of P3V8 predicted by PEP-FOLD[23], where the peptide preferentially adopts a coil conformation stabilized by a network of hydrogen bonds mediated by the side chain of Asp1. The figure was prepared using PyMol[40].

The observation that favorable entropic change contributes to P3 interaction with expanded CAG RNA suggests that the peptide may have undergone conformational changes upon binding to RNA. Structure prediction of the P3 peptide using the PEP-FOLD server[23] suggested that although P3 does not adopt a well-defined tertiary structure, it may preferentially adopt a loosely folded coil conformation that positions the pharmacophores Lys3, Tyr9, and Phe12 on the same surface of the peptide, which may in turn facilitate the recognition and interaction of RNA (FIG. 6). Such conformation is maintained partially by a network of interaction mediated by the side chain of Asp1. To test whether the orientation of Asp1 is important, it was restricted by substituting Gly2 with D-alanine (P3V1). The result shows that the binding affinity of P3V1 was improved by 4-fold which gave a $K_D$ of 2 $\mu M$. Such improvement could be due to better stabilization of the RNA-interacting surface via the restriction of Asp1 or because the replacement of Gly by D-Ala minimized the entropic loss upon binding by restricting the flexibility of the peptide. Analysis of the ITC results reveals that the change in the Gibbs free energy of P3V1 mainly originated from a favorable gain in enthalpy, indicating that the former scenario is more likely. Considering that both Phe12 and Lys13 are important for RNA binding, the 13-mer P3 as was kept the minimal construct for further studies.

To improve the binding affinity and specificity of P3 toward expanded CAG RNA, we performed amino acid substitutions at individual pharmacophores using natural amino acids with similar properties, i.e. Tyr and Phe to other aromatic side chains; Lys to Arg (Table 1). Substitution of Tyr9 with the larger Trp side chain (P3V2) resulted in a lower $K_D$ of 2.2 $\mu M$ and the substitution of Phe with less hydrophobic Tyr (P3V3) and Trp (P3V4) also improved the binding of peptide to expanded CAG RNA by nearly 2- to 4-fold, respectively. These results indicate that although alterations of the size or polarity of the aromatic residues improved the binding affinity of P3, only modest improvements were obtained. On the other hand, the $K_D$ value of P3V5, in which Lys3 and Lys5 both mutated to Arg residues, was approximately 0.86 μM, reflecting a nearly 10-fold improvement over the P3 peptide. Contrarily, when we mutated all three Lys to Arg (P3V6), the $K_D$ of the peptide increased to 23 μM, indicating that the replacement of the amine of Lys13 with a guanidinium is not favored.

Termini Modifications Improve P3 Activity

Next, it was explored whether modifications at the N- and C-termini could improve the binding and inhibitory activity of P3. N-terminal acetylation and C-terminal amidation neutralize the charges at both ends of the peptide and we speculated that it may increase its biological activity. The C-terminal amide was incorporated by solid-phase synthesis of the peptide on a Rink amide linker, while the N-terminal modifications were introduced after assembly of the peptide and before acidolytic release of the completed structure. The $K_D$ value of P3V7 was determined to be 2 μM using ITC, indicating that C-terminal amidation improved the peptide affinity to expanded RNA. When the N-terminus was also acetylated, the dissociation constant of P3V8 was further lowered to 0.33 μM (Table 1). Based on these observations, P3V9 was further synthesized, which combined the modifications of P3V8 and P3V5 (N-acylation, C-amidation and Lys-to-Arg mutation) with the hope to further improving the binding affinity of the peptide. Surprisingly, the binding affinity of the new peptide was not improved, as the $K_D$ value was 2.3 μM (Table 1). It was next investigated whether substitution of Lys3 and Lys5 with other non-natural Lys and Arg analogs would improve the activity of P3V8. The homologated Arg analog, homoarginine (hArg), and two shortened Lys analogs, ornithine (Orn) and 2,3-diaminopropionic acid (Dap), were used for substitution in our studies (Table 5, P3 variants 14-19 respectively). The results reveal that when either Lys3 or Lys5 was replaced by any of the amino acid analogs, no binding could be detected between the P3 variant and the expanded CAG RNA using ITC. This indicates that the chain length of Lys in P3V8 is crucial for its bioactivity. In addition, the linear dimer of P3V8, which has two copies of the peptide in close vicinity, did not show any binding (Table 5, P3V20 and P3V21). The abolishment of the bioactivity may be due to steric hindrance.

To test whether P3V8 specifically targets expanded CAG RNA, ITC experiments were performed using unexpanded CAG RNA ($MJD_{CAG27}$ RNA), expanded CAG RNA ($MJD_{CAG78}$ RNA), and expanded CAA/G RNA ($MJD_{CAA/G78}$ RNA), respectively, to investigate whether the binding of P3V8 is RNA expansion-dependent and sequence-dependent (Table 6). These results demonstrate that P3V8 bound unexpanded RNA or expanded CAA/G RNA with nearly 6-9-fold lower affinity, which indicates that P3V8 is expanded CAG RNA-specific.

Figure 1D:
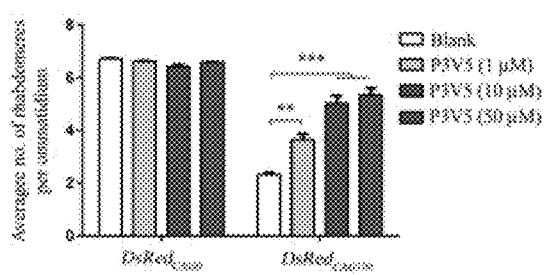

P3 Derivatives Showed Improved Suppressive Effects on PolyQ Neurodegeneration In Vivo Given that P3V5 and P3V8 bind expanded CAG RNA with significantly higher affinities than P3, their inhibitory activities against polyQ neurodegeneration were next tested in vivo. It was previously demonstrated that the full-length MJD CAG transgenic Drosophila model, $flMJD_{CAG27/84}$, can be used to investigate the suppression effects of synthetic peptide inhibitors on both expanded RNA and polyQ protein toxicities[21]. Here the $DsRed_{CAG0/100}$Drosophila model was utilized to investigate the suppressive effects of the P3 analogs on RNA toxicity. In this model, the CAG repeat is located in the 3' untranslated region of the DsRed reporter gene-=. The transcribed expanded CAG RNA is not translated into polyQ protein, and thus the toxicity is solely attributed to the expression of $DsRed_{CAG100}$ RNA. In brief, the expression of expanded CAG RNA causes severe retinal degeneration in the animal that can be quantified by a pseudopupil assay[7]. Inhibitors that can suppress neurotoxicity will result in the recovery of the number of rhabdomeres within the ommatidium. To test the derivatives, third instar larvae were fed different amounts of peptide dissolved in sucrose solution for 2 hr and then allowed to culture in standard fly food until the flies were 12 days old, at which time they were sacrificed for the pseudopupil assay. It was observed that treatment with 50 μM of P3 peptide moderately suppressed neurotoxicity in $DsRed_{CAG100}$ flies (pseudopupil score, 3.74±0.05; FIGS. 1a and b). In contrast, derivatives P3V5 and P3V8 both significantly suppressed neurotoxicity and recovered the number of rhabdomeres with much greater efficiency (FIG. 1c-f). In particular, P3V8 displayed a high level of potency against the neurotoxicity in $DsRed_{CAG100}$ flies and achieved a pseudopupil score of 4.32±0.25 in comparison to P3V5's score of 3.64±0.22 after 1 μM treatment (FIGS. 1d and f). Based on the results from the ITC experiments and pseudopupil assay, the peptide derivative P3V8 is deemed to be the most potent P3 variant that exerts inhibitory activity against expanded CAG RNA-induced neurotoxicity.

Figure 2:
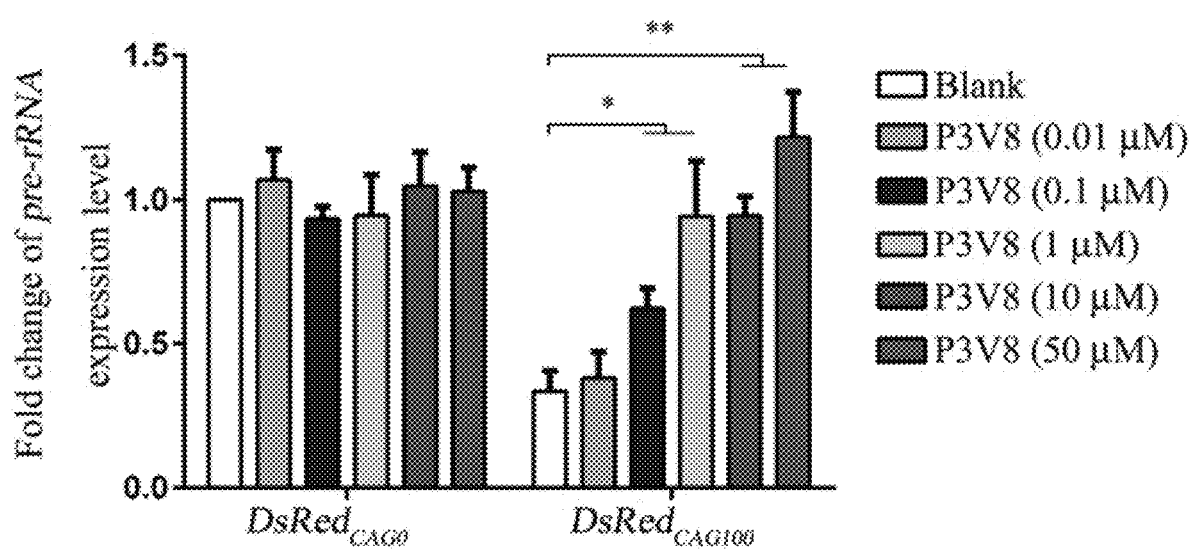
FIG. 2 Treatment of P3V8 peptide suppresses nucleolar stress in vivo. Treatment of P3V8 restored pre-rRNA levels in DsRed$_{CAG100}$ flies. Real-time PCR was performed to determine the levels of pre-rRNA. Data are presented as fold change of the relative pre-rRNA expression levels compared with the blank. Experiments were repeated at least 3 times, and data are expressed as mean±S.E.M. *Indicates P<0.05 and **indicates P<0.01.

P3V8 Restored Pre-rRNA Expression Level in Fly Model Expressing Expanded CAG RNA Ribosomal RNA (rRNA) synthesis occurs within the nucleolus[15]. It was previously shown that expanded CAG RNA induces nucleolar stress by preventing the nucleolar protein NCL from binding to the upstream control element of the rRNA promoter, leading to the downregulation of rRNA transcription[13]. To investigate whether P3V8 suppressed neurotoxicity by alleviating expanded CAG RNA-induced nucleolar stress in vivo, the expression levels of pre-rRNA in were measured $DsRed_{CAG100}$ flies treated with the peptide. Real-time PCR analysis showed that P3V8 could restore the transcript level of pre-rRNA in a dose-dependent manner. When $DsRed_{CAG100}$ flies were treated with 1 μM of P3V8, the pre-rRNA level was fully recovered to the $DsRed_{CAG0}$ control level (FIG. 2). This confirms that P3V8 subdued polyQ neurodegeneration in vivo by effective mitigation of the expanded CAG RNA-induced nucleolar stress.

Figure 3A:
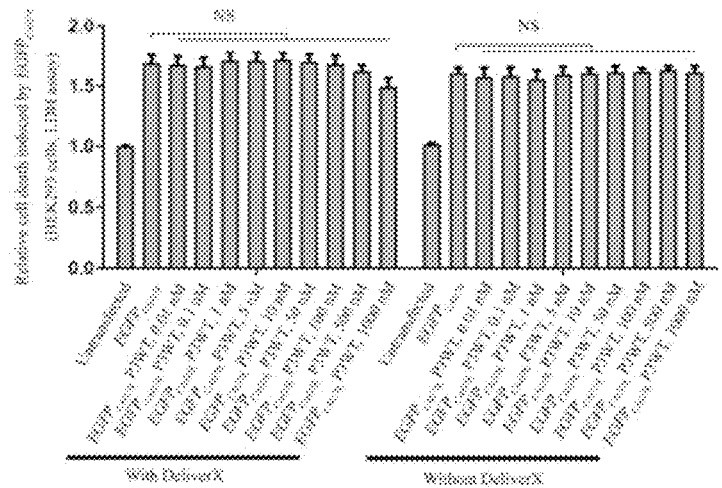
FIGS. 3A-3C P3V8 effectively inhibits cytotoxicity induced by expanded CAG RNA in vitro.
Figure 3B:
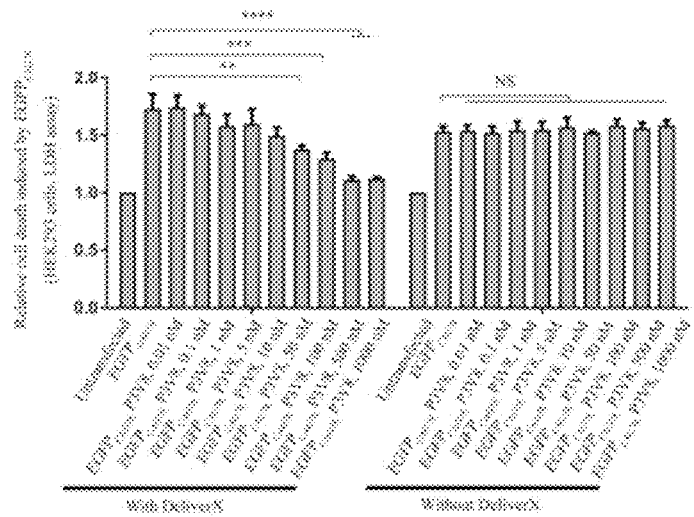
Figure 3C:
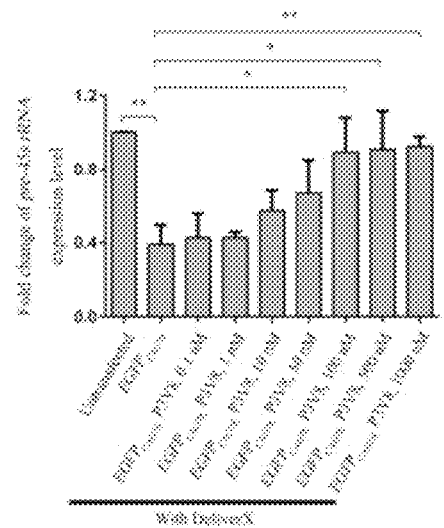

P3V8 Suppressed Expanded-CAG RNA-Induced Cell Death by Modulating rRNA Transcription In Vitro It was next investigated whether P3V8 could also mitigate expanded CAG RNA-induced toxicity in mammalian cells. Overexpression of $EGFP_{CAG78}$ RNA in HEK293 cells has been shown to induce nucleolar stress and apoptosis[21]. To compare the inhibitory activity of P3WT and P3V8, the peptide transfection reagent DeliverX (DX) was used to deliver P3WT and P3V8 to $EGFP_{CAG78}$ RNA-expressing HEK293 cells. FIG. 3A shows that irrespective of the addition of DX transfectant, treatment of P3WT lower than 1 μM did not elicit any significant suppression effect on expanded CAG RNA-induced cell death. Although P3V8 alone did not exert any cellular effect, its administration with the aid of DX could effectively alleviate the cytotoxicity induced by expanded CAG RNA (FIG. 3B). To confirm that P3V8 inhibited expanded CAG RNA-mediated nucleolar stress, the levels of pre-45s rRNA were measured in $EGFP_{CAG78}$ RNA-expressing cells with or without treatment of P3V8 (FIG. 3C). Overexpression of the expanded CAG RNA reduced the level of pre-45s rRNA to approximately 40% of the untransfected control. Upon P3V8 treatment, a dose-dependent restoration of pre-45s rRNA level was observed (FIG. 3C). Taken together, these results demonstrate that P3V8 could effectively mitigate expanded CAG RNA-induced nucleolar stress and neutralize the cytotoxic effect.

Assessment of P3V8 Toxicity

Figure 1E:
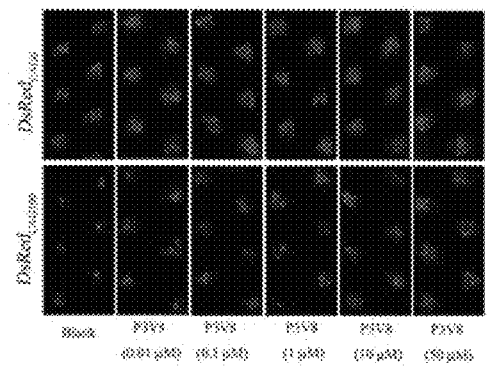
Figure 1F:
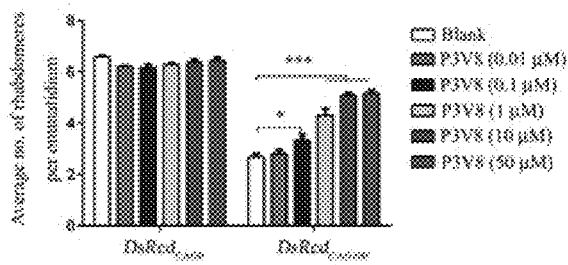
Figure 7:
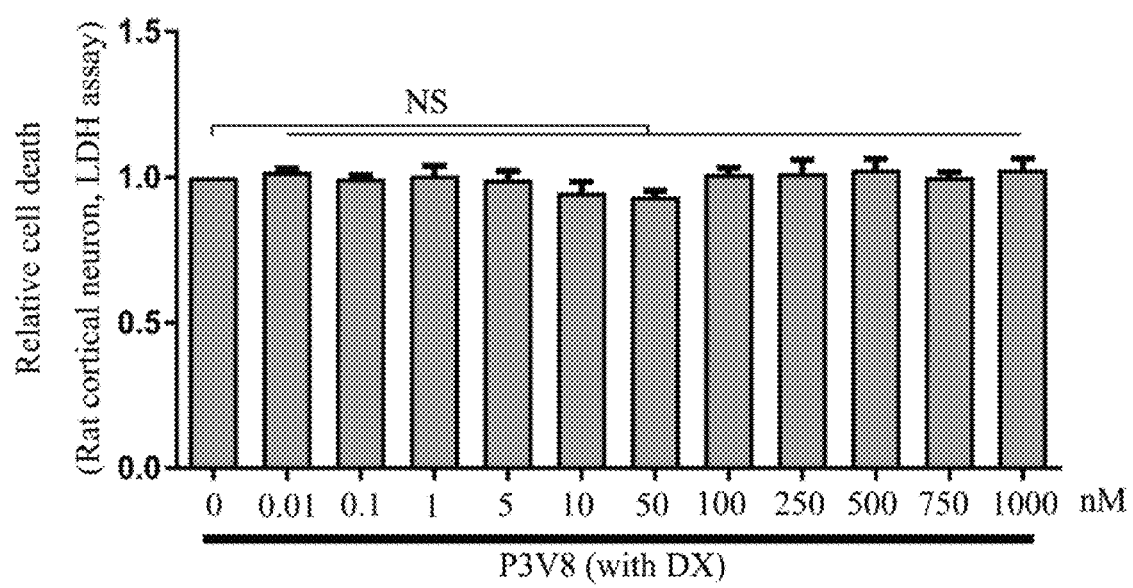
FIG. 7 Treatment of P3V8 causes no cytotoxicity in primary rat cortical neurons. A density of 5×10$^5$ of primary rat cortical neurons were seeded on culture dish and individually cultured in medium containing 0.01, 0.1, 1, 5, 10, 50, 100, 250, 500, 750, and 1000 nM of P3V8 peptide (transfected with DeliverX). The lactate dehydrogenase (LDH) cytotoxicity activity was measured 72 hr post-treatment. Fold change of LDH activity was normalized to untreated cells. Data are expressed as mean±S.E.M. for 3 independent experiments. NS indicates no significance.

Because of the aim to develop P3V8 into a potent inhibitor that targets RNA toxicity in degenerating cells within the nervous system, it was assessed whether P3V8 had deleterious effects on neuronal cells by determining lactate dehydrogenase release in the culturing medium of rat cortical neurons. After incubation of P3V8 in concentrations ranging from 0.01 nM to 1 µM for 72 hr, no significant cell death was observed in the P3V8-treated neurons when compared to the untreated control (FIG. 7). It should be noted that the peptide also did not show any observable effect when DsRed$_{CAG0}$Drosophila was treated with P3V8 at up to 50 µM (FIGS. 1E and 1F). This indicates that P3V8 exhibits low cytotoxicity both in vitro and in vivo.

N-Terminally Acylated P3V8 Showed Enhanced Cellular Uptake

Figure 4A:
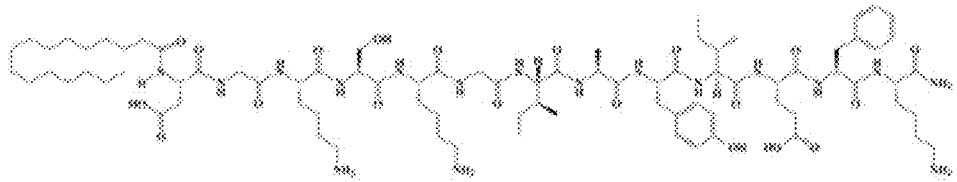
FIGS. 4A-4E L1P3V8 effectively inhibits neurodegeneration induced by expanded CAG RNA in vitro and in vivo.
Figure 4B:
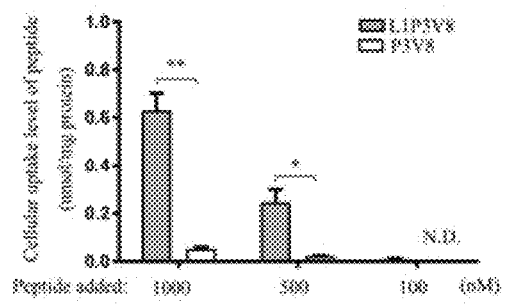
Figure 4C:
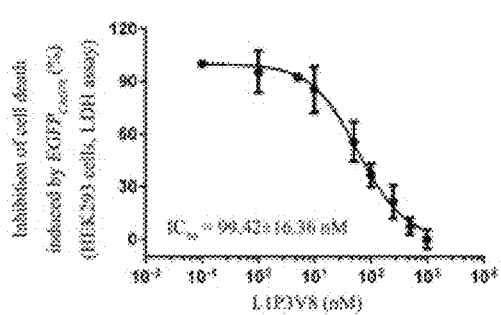
Figure 4D:
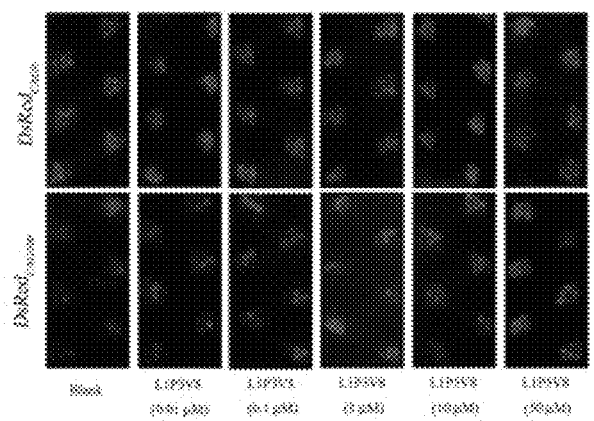
Figure 4E:
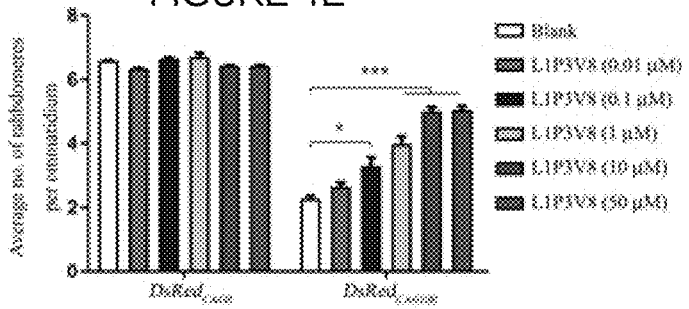
Figure 8:
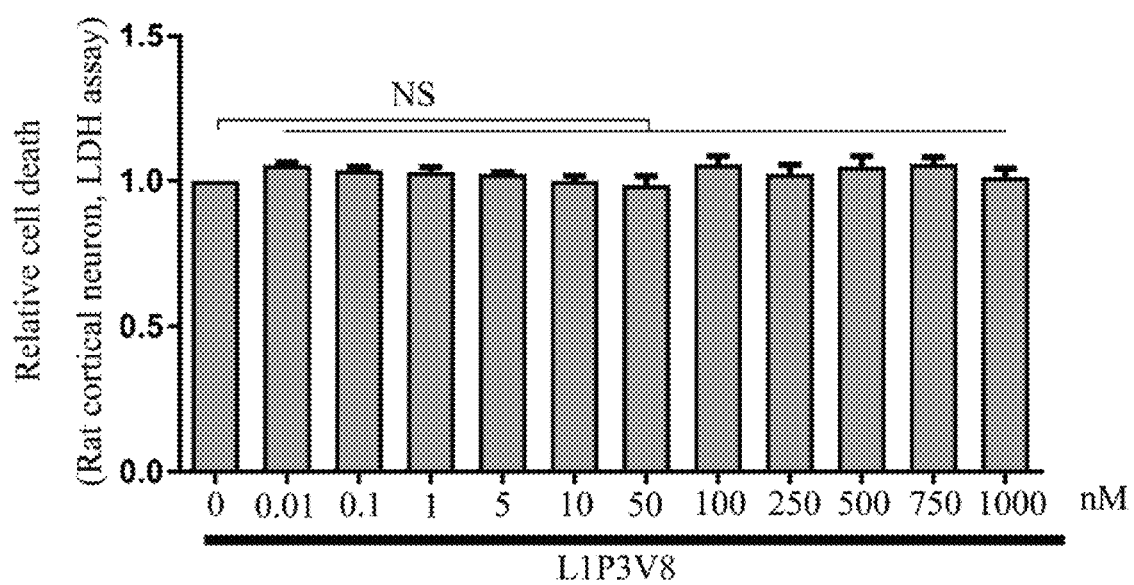
FIG. 8 Treatment of L1P3V8 causes no cytotoxicity in primary rat cortical neurons. A density of $5\times10^5$ of primary rat cortical neurons were seeded on culture dish and individually cultured in medium containing 0.01, 0.1, 1, 5, 10, 50, 100, 250, 500, 750, and 1000 nM of L1P3V8 peptide. The LDH cytotoxicity activity was measured 72 hr post-treatment. Fold change of LDH activity was normalized to untreated cells. Data are expressed as mean±S.E.M. for 3 independent experiments. NS indicates no significance.
Figure 9:
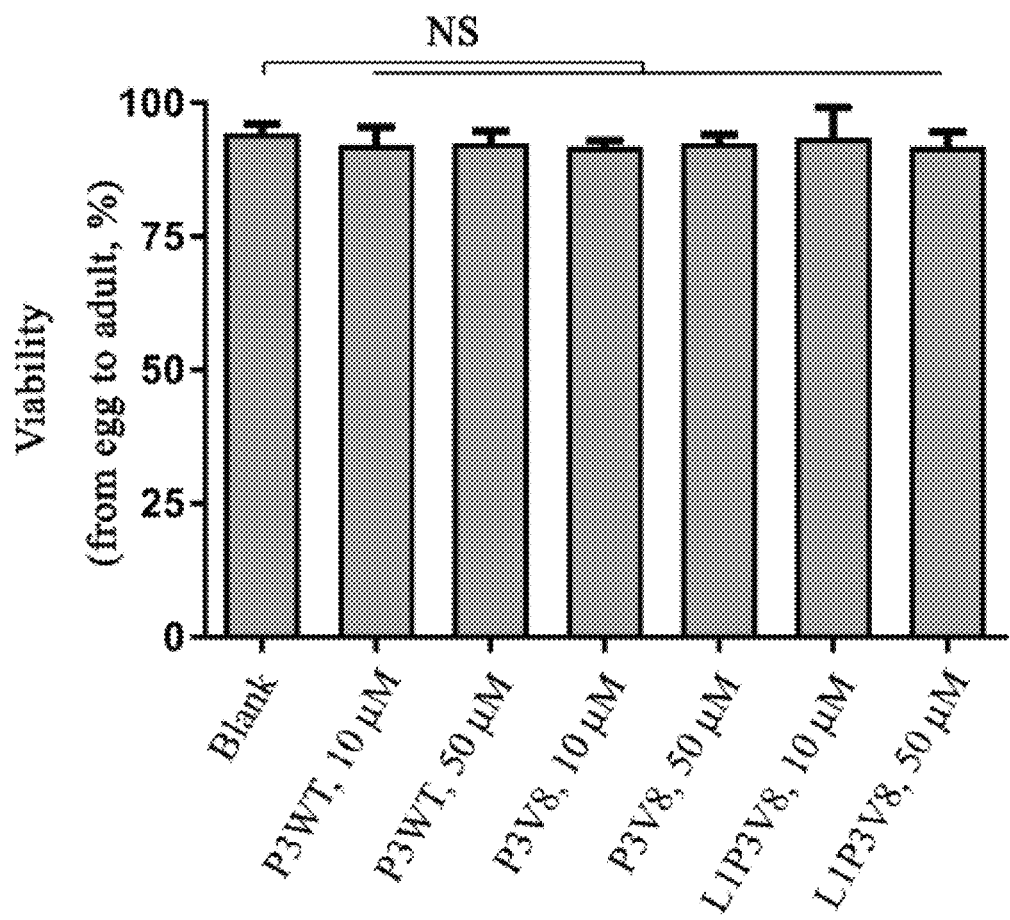
FIG. 9 Treatment of P3WT, P3V8 and L1P3V8 did not affect the viability of wild type Drosophila from egg to adult. Eggs laid within 5 hr were collected and cultured in fly food containing 10 or 50 μM of respective peptides at 21.5° C. Viability from egg to adult was calculated as the number of adult flies collected divided by the number of eggs examined. Data are expressed as mean±S.E.M. for 3 independent experiments. NS indicates no significance.

Acylation of peptides with long-chain lipids has been shown to improve their cellular uptake, in vivo half-life, and membrane permeability and to change their pharmacokinetic properties[24,25,26]. Importantly, lipid solubility is a key factor for the transportation of inhibitors across the blood-brain barrier. It was therefore investigated whether acylation of P3V8 could improve its cellular uptake in vitro as well as bioavailability both in vitro and in vivo. The L1P3V8 peptide was generated by introducing palmitic acid N-terminally to P3V8 in place of N-acetylation (FIG. 4A). LC/MS was used to detect the level of P3V8 or L1P3V8 uptaken by HEK293 cells after 3 hr treatment. FIG. 4B shows that higher cellular concentration of L1P3V8 was measured in HEK293 cells when compared to that of P3V8 in both 500 nM and 1 µM treatment groups. While a low cellular concentration of L1P3V8 in HEK293 cells treated with 100 nM of peptide could be detected, no uptake of P3V8 was detected (FIG. 4B). These data collectively demonstrated that the lipidation of P3V8 improved peptide cellular uptake. L1P3V8 was next administered to EGF-P$_{CAG78}$ RNA-expressing HEK293 cells without any DX peptide transfecting reagents to determine whether lipidation can facilitate the cellular uptake of the peptide. As shown in FIG. 4C, L1P3V8 alone effectively inhibited expanded CAG RNA-induced cell death with an empirical IC$_{50}$ value of ~100 nM. In addition, L1P3V8 showed no cytotoxic effects on rat cortical neurons and DsRed$_{CAG0}$Drosophila model, and no obvious alteration in egg-to-adult viability of wild type flies (FIGS. 8 and 9, FIG. 4C). Treatment of DsRed$_{CAG100}$Drosophila with L1P3V8 also suppressed retinal degeneration (FIGS. 4D and 4E). These findings indicate that lipidation of P3V8 improved its cell penetration properties without affecting its inhibitory activity.

Lipidation Improved P3V8 In Vivo Stability

To test whether lipidation could also improve the stability of P3V8, the stabilities of P3V8 and L1P3V8 were compared in rat plasma and brain homogenate via in vitro incubation to estimate their extent of degradation in plasma and brain tissues. The results shown in Table 2 indicate that the stability of L1P3V8 in both rat plasma and rat brain homogenate at 37° C. was significantly improved in comparison to that of P3V8. At the concentration of 2000 ng/mL, only 21% and 3% of P3V8 remained stable in plasma and brain homogenates, respectively, whereas nearly all L1P3V8 remained intact in plasma and around 45% of L1P3V8 could be detected in the brain homogenate after 1 hr of incubation. When the incubation was extended to 3 hr, around 87% and 21% of L1P3V8 were still detectable in the plasma and brain homogenates, respectively, whereas P3V8 was almost completely degraded. Such improved stability of L1P3V8 was also observed in plasma when the experiments were repeated using 1000 ng/mL and 500 ng/mL of L1P3V8. Because the concentrations of both P3V8 and L1P3V8 after incubation at 500 ng/mL with brain homogenates were below the limit of quantitation (LOQ), no conclusion on comparison of their stabilities in brain homogenate could be drawn. Nonetheless, these results demonstrate that lipidation of P3V8 with palmitic acid significantly improved its stability in different biological matrices.

In Vivo Pharmacokinetic Properties and Brain Uptake of P3V8 and L1P3V8

Figure 5A:
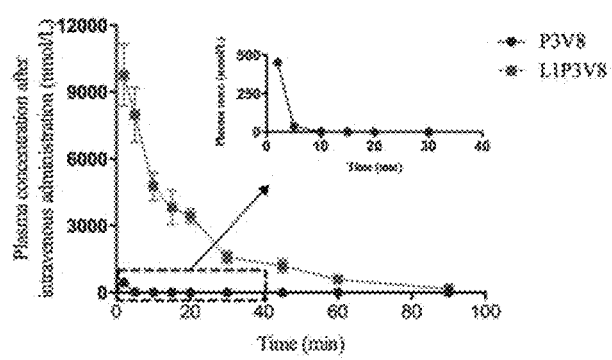
FIGS. 5A-5D In vivo pharmacokinetic study and brain uptake of 3 μmol/kg P3V8 or L1P3V8 in rats.
Figure 5B:
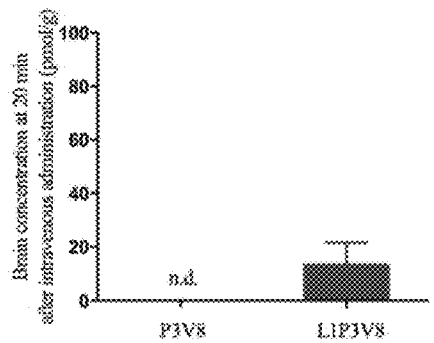
Figure 5C:
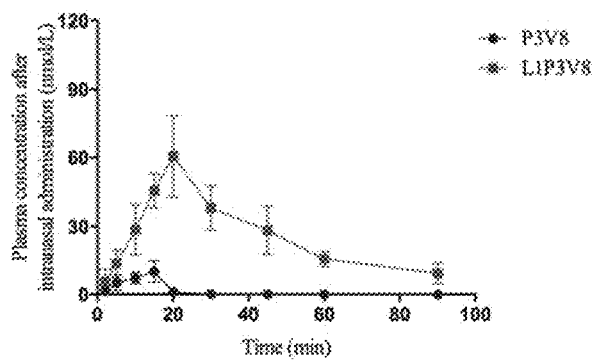
Figure 5D:
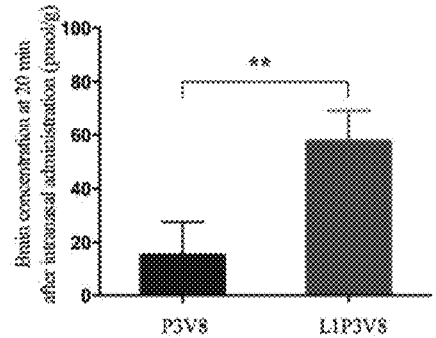

The plasma concentration versus time profiles of P3V8 and L1P3V8 after intravenous administration at 3 µmol/kg in Sprague Dawley (SD) rats were studied and compared (FIG. 5A and Table 3). Without lipidation, P3V8 was quickly eliminated in the plasma 10 min after administration and its half-life was too short to be determined. In contrast, L1P3V8 had a significantly longer half-life of 17 min (Table 3) and remained quantifiable at 190 nmol/L in the plasma 90 min after dosing (FIG. 5A). The maximum observed drug concentration ($C_{max}$) and integrated time-concentration responses (area under the curve, AUC) of L1P3V8 were also significantly higher than that of P3V8 (Table 3), indicating better plasma stability after lipidation. The ability of P3V8 and L1P3V8 to be taken up by the brain was also analyzed after intravenous bolus injection. It was noticed that no P3V8 and 13 pmol/g L1P3V8 was detected in the rat brain 20 min after administration (FIG. 5B), suggesting that intravenous administration might not be suitable for brain delivery of these peptides. These undesirable pharmacokinetic properties led to explore an alternative route of delivery of these peptides to the brain. One of the options is intranasal administration. Intranasal delivery involves the externally exposed olfactory or trigeminal nerve systems and thus is the most direct method of noninvasive delivery method to the brain[27]. Both P3V8 and L1P3V8 were administered intranasally into SD rats at a dose of 3 µmol/kg with pretreatment of 0.5% mucoadhesive chitosan. The pharmacokinetic profiles obtained are significantly different from those obtained after intravenous administration (FIG. 5C and Table 3). It was noted that the plasma levels of the intranasally administered inhibitors were significantly lower than that from intravenous administrations. The concentration of P3V8 in plasma peaked at 15 min and diminished rapidly within 20 min, whereas L1P3V8 concentration peaked at 18 min and remained stay around 9 nmol/mL at 90 min. Similar to the observations from intravenous administration, both $C_{max}$ and AUC of L1P3V8 were significantly higher than those of P3V8 after intranasal administration, which clearly demonstrates again that lipidation of the inhibitor increased its systemic exposure. In addition, significantly higher concentrations of L1P3V8 (58 pmol/g) and P3V8 (15 pmol/g) in the brain were achieved 20 min after intranasal dosing, as compared to those from intravenous administration, indicating better brain uptake via the intranasal route (FIG. 5d). Taken together, these findings support that the combined strategies of lipidation and intranasal administration significantly improve the pharmacokinetic properties and brain uptake of our peptide inhibitor.

Substitution by PNA

In addition to substitution of the pharmacophores by natural or non-natural amino acids, substitution by synthetic peptide nucleic acids (PNA) was also explored to improve the binding affinity and specificity of P3 (Table 7). In this application, PNA is an artificially synthesized polymer that mimics deoxyribonucleic acids (DNA) and ribonucleic acids (RNA). The backbone of PNA is composed of N-(2-aminoethyl)-glycine that forms peptide bonds with amino acids. In Table 7, aPNA and gPNA denote that the purine bases adenine and guanine are linked to the backbone of PNA respectively. cPNA and tPNA denote that the pyrimidine bases pyrimidine bases cytosine and thymine are linked to the backbone of PNA respectively. * denotes the location and number of amino acids that was removed at the corresponding position of P3. The results revealed that when P3 was modified by C-terminal amidation, the addition of tPNA at the N-terminus improved the $K_D$ to 2.2 µM (P3V10). When two amino acids, Asp and Gly, at the N-terminus of P3 were removed, the addition of tPNA (P3V11) or cPNA (P3V24) significantly improved the $K_D$ to 0.12 µM and 0.96 µM respectively. These results indicate that the addition or substitution of PNA may provide a new mean to improve the binding and specificity of P3, likely through base pairing interaction with the bases of the expanded RNA.

Discussions

Despite the growing knowledge of the role of RNA transcripts in the pathological mechanisms of polyQ diseases, there is a lack of inhibitors that can counteract their neurotoxicity. On the basis that sequestration of NCL by expanded CAG RNA induces cytotoxicity, a peptide inhibitor P3 was recently developed that disrupts NCL-RNA interaction and consequently mitigates RNA toxicity in polyQ diseases. In this study, the equilibrium dissociation constant $K_D$ of P3 was determined using ITC, and it was discovered that the binding of P3 to RNA is both enthalpically and entropically favored. Short peptides like the 13-mer P3 usually assume flexible conformations in an aqueous solution and therefore suffer entropic loss upon binding to their targets. The finding that P3 binds expanded RNA with a favorable T$\Delta$S suggests that P3 may have undergone a conformation change upon binding to the RNA in solution.

When characterizing the effects of Ala substitutions of the pharmacophores of P3 on its interaction with expanded CAG RNA, the inventors found that the basic Lys residues are more important than the aromatic residues in the interaction with expanded RNA. Substitution of any of the three Lys in P3 greatly reduced its binding affinity to RNA, indicating that electrostatic interactions play a dominant role in the affinity of P3. This is no surprise because CAG-repeat RNA duplex adopts an A' helical conformation that is intermediate to the A- and B-forms of nucleic acids and is highly electronegative on its surface and thus charge-complementary with the key pharmacophores of P3. As described above, the substitution of Lys at positions 3 and 5 by Arg remarkably improved the binding affinity of the peptide by nearly 10-fold (Table 1, P3V5). This observation suggests that the higher pKa of arginine and its guanidinium group may have further strengthened the ionic interaction with the RNA. Surprisingly, when Lys13 was further mutated to arginine, the binding affinity of the peptide was adversely reduced by nearly 3-fold, indicating that the amine group of Lys13, but not the charge alone, is critical for the binding of P3 and RNA. Further research is needed to investigate whether the side chain amine of Lys13 is important for stabilizing the peptide for RNA recognition or for mediating the critical interaction with nucleic acid.

Previous studies have shown that the charge neutralization of the N- and C-termini of synthetic peptides by acetylation and amidation can improve their stabilities in cell cultures and serum, thus improving their biological activity. Based on these findings, P3V8 was generated, which is capped by acetylation and amidation at the N- and C-termini, respectively, in an attempt to improve the biological activity of P3 and in hopes that the same strategy can be applied to other P3 derivatives. It was observed that capping of both termini of P3 not only improved its binding affinity to expanded CAG RNA ($K_D$=0.33 µM) but also significantly improved its potency both in vivo and in vitro. In a recent study of compounds that block Alzheimer's AP channel activity, Flora and colleagues showed that capping of the amine and carboxyl groups of free histidine helps to improve the residue activity by preventing nonspecific interaction with other reactive residues in the target[28]. It is speculated that the capping of P3, now termed P3V8, might have exerted a similar effect and prevented nonspecific interaction between the peptide and the RNA's negatively charged surface, thus improving the binding and efficacy of the peptide. Furthermore, the slight increase in pI of the peptide might also have contributed to its better affinity to the electrostatically negative surface of RNA (P3V8, pI=10.02 vs. P3, pI=9.64).

With the success of P3V8, the same capping strategy was applied to P3V5 to further improve its activity. However, as described above, the combination of Lys-to-Arg mutations of residues 3 and 5 and the capping of the peptide termini did not improve the peptide's binding affinity but instead reduced the $K_D$ to about 2.3 µM. it is speculated that upon N- and C-termini modifications, the interactions of the arginines and RNA might have been altered and that P3V9 likely adopts a different binding mode than P3V5 or P3V8. Moreover, the lengths of the basic side chains at residues 3 and 5 also appear to play a determining role in the binding of the peptide, as either lengthening or shortening the basic side chains abolished the interaction between the inhibitors and expanded RNA, suggesting that the distances between the basic side chains and the RNA is critical and that only limited conformational flexibility is allowed after P3V8 binds to the RNA. Such a rigid binding mode of P3V8 is further supported by the observation that tandem repeats of the peptide failed to interact with the expanded RNA. Studies on the conformation and dynamics of P3V8 before and after RNA binding are needed to understand the mechanism of its specific inhibitory activity.

RNAs are becoming more recognized as attractive therapeutic targets because they fold into well-defined secondary and tertiary structures but exhibit a large variety of conformations, which can provide favorable opportunities for specific drug targeting. One interesting feature of the A' form of CAG RNA is the widened major groove caused by the non-canonical AA base pairs[29]. Such widening provides binding sites that are unique to CAG-repeat RNA, and their accessibility may offer opportunity to improve the potency and specificity of our inhibitor. Further structural information on the interaction between P3V8 and CAG RNA will be useful to provide insight into how to make use of such a unique feature. Nevertheless, the results of this study demonstrate that neutralization of the N- and C-termini by simple modifications like acetylation and amidation can have significant effects on the binding and inhibitory properties of peptidyl inhibitor against an RNA target.

In the past few decades, several inhibitors targeting protein toxicity[30,31,32,33] or CAG RNA toxicity[21,34] in polyQ disease have been developed. Some even showed therapeutic potential[30,31, 32,33]. In this study, the present inventors demonstrated for the first time a structural activity relationship (SAR) investigation of the peptidylic inhibitor, P3, toward CAG RNA toxicity in polyQ diseases. The SAR study led us to identify a more potent peptide derivative of P3, P3V8, which shows dramatically improved inhibitory efficacy against expanded RNA-mediated toxicity in vivo. However, many peptides have short half-life in vivo, typically in minutes, which raises concern whether P3V8 could be administered as a therapeutic agent. Previous studies have established that covalent anchoring of lipids to peptides promotes peptide binding to the fatty acid binding sites on albumin-. As albumin has a very long half-life, this 'docking' into albumin can significantly extend the functional half-life of peptides. Furthermore, it is speculated that lipidation of a peptide could improve the ability to cross cell membranes and enter cells. P3V8 was therefore lipidated by N-acylation with palmitic acid. Stability studies of the lipidated peptide L1P3V8 in plasma and brain homogenates revealed that lipidation significantly enhanced the cellular uptake and in vivo stability of P3V8. Above all, the lipidation strategy notably improved the pharmacokinetic profile and brain uptake of L1P3V8 in rats when it was administered intranasally, conferring our inhibitor drug/lead-like properties. The ability of therapeutic agents to pass the blood-brain-barrier is one of the most critical requirements for treatment of neuronal diseases. Although the mechanism of brain uptake of L1P3V8 remains to be elucidated, these results illustrate that the combination of lipidation and intranasal administration may provide a new means to improve the brain uptake of therapeutic agents. In conclusion, the results provide proof of concept that lipidated peptidyl inhibitors that target RNA toxicity are a novel therapeutic option for polyQ diseases. Further modification and optimization on this lead-like L1P3V8 will be needed to prolong its half-life and uptake level in the brain.

Methods

Peptide Modeling

Molecular modeling of P3V8 was carried out using the online PEP-FOLD 2.0 server[23]. The sequence of the 13-amino acid peptide was submitted to the server and 100 simulations were performed using the default settings. The program returned the most representation conformations identified in terms of energy and population, and clustered them based on their sOPEP (Optimized Potential for Efficient structure Prediction) coarse grained energies. The representative model of the top-ranked cluster with the lowest sOPEP energy values was selected for this study.

Construction of Plasmids

The pcDNA3.1-MJD$_{CAG27}$, pcDNA3.1-MJD$_{CAG78}$, pcDNA3.1-MJD$_{CAA/G78}$ and pEGFP$_{CAG78}$ constructs were reported previously[7,13].

Synthesis of Peptides and CAG RNAs

P3WT and P3 mutant (MT) peptides were purchased from GenScript USA Inc. All other peptide variants were prepared by Fmoc solid-phase peptide synthesis on automated peptide synthesizers, Biotage Syro Wave and Biotage SP Wave instruments, and assembled on a 0.1 mmol scale, unless noted otherwise. Peptide syntheses were carried out on a TentaGel S Rink Amide resin (0.22 mmol/g). Amino acids had Fmoc protection of $N^\alpha$-amino groups; side-chain protecting groups were tert-butyl (Tyr, Glu, Asp), 2,2,4,6,7-pentamethyl-dihydrobenzofuran-5-sulfonyl (Pbf, for Arg and hArg), and tert-butyloxycarbonyl (Boc, for Lys, Orn and Dap). Amino acids, NMP, DMF and piperidine were supplied by Iris Biotech (Germany). Acetonitrile, formic acid, triethylsilane (TES), trifluoroacetic acid (TFA) acetic anhydride, and dichloromethane (DCM) were from Sigma-Aldrich (Denmark). All chemicals were used as received and without further purification.

Analytical HPLC was performed with a Dionex Ultimate 3000 instrument on a Phenomenex Germini-NX C18 column (3 μm, 50×4.6 mm), column oven thermostated to 42° C., and a linear gradient flow of $CH_3CN$—$H_2O$ (0.1% formic acid), connected to an ESI-MS (MSO Plus Mass Spectrometer, Dionex). Purification of the peptide was performed on a preparative Dionex Ultimate 3000 HPLC with a C18 column Phenomenex Gemini Axia (5 μm, 100×21.2 mm, 110 Å). Unless otherwise stated $CH_3CN$—$H_2O$ (0.1% TFA or 0.1% formic acid) was used as eluent with a flow of 15 mL/min. Gradient elution for 0-5 min was 5%, then to 55% for 5-32 min.

All standard Fmoc amino acids were coupled in DMF with 5.2 equivalents of amino acids and HOAt, with 5 equivalents of HBTU and 9.4 equivalents DIEA. The coupling time was 60 min at room temperature. All non-standard amino acids, as well as palmitic acid, were coupled using 2 equivalents of amino acids and HOAt, 1.9 equivalents of HBTU and 3.6 equivalents DIEA. Coupling times were 10 min at 75° C. N-terminal fatty acid was introduced using the same conditions as for the coupling of standard amino acids.

In the synthesis of peptides P3V7 to P3V21, the first 10 couplings used a coupling time of 60 min at 25° C. with NMP and washings in-between couplings. Deprotections were performed by treatment with piperidine-DMF (2:3) for 3 min, followed by piperidine-DMF (1:4) for 15 min. After each coupling and deprotection, a washing procedure with NMP (3×), DCM (1×), then NMP (3×) was performed. From the 10th coupling onwards, the coupling time was increased to 2×120 min and an extra deprotection step (15 min) with piperidine-DMF (1:4) was added. The N-terminal acetylation was achieved with acetic anhydride in DMF (1:4) for 2×15 min. After completion of peptide chain assembly, the resin was washed 6 times with DCM. All the peptides were released and deprotected by treatment with a cocktail of trifluoroacetic acid (TFA), triethylsilane (TES) and $H_2O$ (95:2:3 or 95:2.5:2.5) for 2 hr. The TFA solutions were concentrated under a flow of nitrogen and the compounds were precipitated with diethylether to yield the crude products. All peptides were purified by RP-HPLC.

The sequences of peptides are listed in Table 1, Tables 4 and 5. The purity of peptides used in cell experiments and in vitro binding was over 90%. Desalted peptides were used in Drosophila feeding assays. All RNAs were synthesized using the MEGAscript® kit (Ambion) as previously described[13], and the MJD$_{CAG27}$, MJD$_{CAG78}$ and MJD$_{CAA/G78}$ RNAs were transcribed from linearized pcDNA3 CAG constructs.

Isothermal Titration Calorimetry Binding Assay

Experiments were carried out using a MicroCal iTC200 isothermal titration calorimeter (GE Healthcare) at 25° C. Data were analyzed using the Origin® scientific plotting software version 7 (Microcal Software Inc.). All RNAs and peptides were dissolved in binding buffer (20 mM MOPS, pH 7.0; 300 mM NaCl) and 0.7 mM of peptide was titrated into 0.5 μM of RNA for each experiment. The concentration of RNA was estimated with appropriate extinction coefficients at 260 nm on a Nanodrop 2000 (Thermo Scientific). A reference power of 8 μcal/s was used with an initial 0.5 μl of injection of peptide followed by 2 μl for all subsequent titrations points with a 60 sec initial equilibrium delay and 150 sec pause between injections. The samples were stirred at a speed of 1000 rpm throughout the experiment. The thermal titration data were fitted to the 'one binding site model' to determine the dissociation constant ($K_D$). Each experiment was repeated at least 3 times with consistent results obtained.

Cell Culture, Plasmid Transfection and Peptide Transfection

HEK293 cells were cultured at 37° C. with 5% $CO_2$ in DMEM supplemented with 10% FBS and 1% penicillin-streptomycin. Primary rat cortical neurons were isolated and cultured as previously described[37]. Transient transfection of HEK293 cells was performed using Lipofectamine 2000 (Life Technologies). P3V8 were delivered to HEK293 cells using the DeliverX (DX) Peptide Transfection Kit (Affymetrix) 4 hr after DNA transfection. At least two batches of independently synthesized peptides were used in the experiments.

Lactate Dehydrogenase (LDH) Cytotoxicity Assay and $IC_{50}$ Determination

To detect the effect of P3V8 and lipidated P3V8 (L1P3V8) on inhibiting cell death in $EGFP_{CAG78}$ RNA-expressing HEK293 cells, a LDH assay was employed. HEK 293 cells were seeded on a 24-well plate at a density of $0.5 \times 10^5$, and $pEGFP_{CAG78}$ DNA construct was used to transfect the cells. For P3V8 treatment, different concentrations of P3V8 as indicated in the figure were transfected by DeliverX transfectant 4 hr after DNA transfection. For L1P3V8 treatment, different concentrations of L1P3V8 were added into individual wells immediately after DNA transfection. Seventy-two hours after treatment, LDH enzyme activity in the cell culture medium was measured as described before. Experimental groups were normalized to the untransfected control. After normalization, data were analyzed using the dose response-inhibition curve (nonlinear regression-variable slope) to determine the $IC_{50}$ value (Prism6 software, GraphPad Software, Inc.). Each experiment was repeated at least 3 times.

Drosophila Genetics, Peptide Feeding and Assays

Flies were raised at 21.5° C. on cornmeal medium supplemented with dry yeast. Fly lines bearing $UAS-DsRed_{CAG0}$ and $UAS-DsRed_{CAG100}$ were kind gifts of Professor Nancy Bonini (University of Pennsylvania, USA). The gmr-GAL4 fly line was obtained from Bloomington Drosophila Stock Center. For pseudopupil assay, third instar larvae were fed with various amount of respective peptides dissolved in 2% sucrose solution for 2 hr and then continued to culture in standard fly food at 21.5° C.[38]. Pseudopupil assay was performed on 12 day-old adult flies as mentioned previously[39]. Images were captured by SPOT Insight CCD camera controlled by the SPOT Advanced software (Diagnostic instruments Inc.). Image processing was performed using the Adobe Photoshop CS software (Adobe). Each experiment was repeated at least 3 times (n=10 fly heads), and consistent results were obtained. For viability test of wild-type flies from egg to adult stage, eggs born within 5 hr were collected and cultured in fly food containing 10 or 50 µM of respective peptides at 21.5° C. Viability from egg-to-adult was calculated as the number of adult flies collected divided by the number of eggs examined. Each experiment was repeated for three times (at least 130 eggs were examined in each group). Two batches of independently synthesized peptides were used in the experiments.

RNA Extraction, Reverse Transcription-PCR and Real-Time PCR

RNA was extracted from cells or ten 12 day-old adult fly heads by Trizol reagent (Life Technologies), and 1 µg of purified RNA was then used for reverse-transcription using the ImPromII™ Reverse Transcription System (Promega). Random hexamer (Roche) was used as primers in reverse transcription. Taqman gene expression assays were performed on an ABI 7500 Real-time PCR system and data were analyzed as previously described[13]. The following probes were used: pre-45s rRNA (Assay ID: AILJIZM), pre-rRNA (Assay ID: AIMSG5U), Drosophila GAPDH (Assay ID: Dm01841186) and human actin (Assay ID: Hs99999903_m1). Each experiment was repeated at least 3 times.

In Vitro Stability Studies in Rat Plasma and Brain Homogenate

Sprague-Dawley (SD) rats (male, 180-200 g) were supplied by the Laboratory Animal Services Centre at The Chinese University of Hong Kong. All animal studies were conducted under the approval of the Animal Ethics Committee of The Chinese University of Hong Kong, and were performed in accordance with relevant guidelines and regulations. Blank rat brain homogenate was prepared by ultrasonic probe homogenization (Micoson XL-2000, Misonix, Framingdale, N.Y., USA) of brains collected from the control rats. Blank rat plasma was prepared by centrifugation (8000 rcf for 3.5 min) of blood collected from control rats. For the stability test, 2000 ng/mL and 500 ng/mL of P3V8 or L1P3V8 was spiked into the blank rat plasma or brain homogenate and vortexed. The mixtures were incubated at 37° C. with 100 rpm in a water bath for 1 or 3 hr. The incubation was terminated by addition twice the volume of acetonitrile and centrifugation at 13000 rcf for 10 min. The supernatant was collected for LC/MS/MS analysis.

Cellular Uptake Studies in HEK293 Cells

HEK293 cells were seeded on a 6-well plate at a density of $6 \times 10^5$ and cultured overnight at 37° C. with 5% $CO_2$ in DMEM supplemented with 10% FBS and 1% penicillin-streptomycin. Cells were then treated with 100, 500 or 1000 nM of respective peptide at 37° C. for 3 hr. After treatment, the cells were washed with ice-cold PBS and then lysed by 2% SDS solution. Aliquot (100 µl) of the cell lysate was added with 200 µl acetonitrile and centrifuged at 13000 rcf for 10 min to precipitate the proteins. The collected supernatant was subjected to LC/MS analysis. The protein concentration of the cell lysate was measured using a bicinchoninic acid protein assay kit following Sigma's protocol.

Plasma Pharmacokinetic and Brain Uptake Studies in SD Rat

SD rats (180-200 g) were anesthetized with an intraperitoneal injection of ketamine (60 mg/kg) and xylazine (6 mg/kg) and received a minor surgery of cannulation with a polythene tube (0.4 mm i.d., 0.8 mm o.d., Harvard Apparatus, Holliston, Mass., USA) in the left jugular vein. The rats received an overnight recovery with free access to food and water. In the following day, rats were administered P3V8 or L1P3V8 (3 µmol/kg) via intravenous or intranasal routes. For intravenous administration, appropriate volume of P3V8 or L1P3V8 (3 µmol/mL, dissolved in water) was injected to the rats via the cannula. For intranasal administration, the rats were temporarily anesthetized by inhalation of carbon dioxide, and was administrated with appropriate volume of P3V8 or L1P3V8 (30 µmol/mL, dissolved in water with 5% PEG400) in both nostrils by a micropipette. Chitosan solution (0.5% w/v, pH 6.5, 20 µL) was pre-treated to rats intranasally 5 min before the P3V8 and L1P3V8 was administrated via intranasal routes. For the pharmacokinetic study, after the drug administration, blood samples were collected from the catheter at appropriate time intervals (2, 5, 10, 15, 20, 30, 45, 60, and 90 min). After each collection, 0.2 mL of saline containing 25 IU heparin was injected to compensate for the blood loss. Plasma was collected after centrifugation at 8000 rcf for 3.5 min and stored at −80° C. until analysis. For brain uptake study, at 20 min, the rat was anesthetized and perfused by 500 mL saline, and the whole brain was collected. The brain was wiped by tissue paper to remove excess water, meninges and blood vessels followed by storage at −80° C. until analysis.

Sample Preparation for LC/MS/MS

Aliquot of plasma sample (80 μL) was mixed with 160 μL acetonitrile. The mixture was vortexed for 1 min and followed by centrifugation at 13000 rcf for 10 min. The supernatant was collect and subjected to LC/MS/MS analysis.

To prepare brain homogenate, the whole brain of each rat was minced. Saline (2 mL/g brain) was added followed by ultrasonic probe homogenization on ice. For analysis of P3V8, aliquot of brain homogenate (100 μL) was mixed with 200 μL acetonitrile. The mixture was vortexed for 1 min and followed by centrifugation at 13000 rcf for 10 min to collect the supernatant. For analysis of L1P3V8, aliquot of brain homogenate (650 μL) was centrifuged at 6000 rcf for 10 min. After the supernatant was collected, 400 μL saline was added to re-suspend the pellet. The mixture was again vortexed for 5 min and centrifuged at 6000 rcf for 10 min. The supernatant collected was loaded to a preconditioned Oasis® HLB cartridges (Waters, Mass., USA). After washed with 1 mL of 10% acetonitrile in water, the analyte was eluted with 0.25 mL 95% acetonitrile in water.

LC/MS/MS Analysis

Agilent 6430 Triple Quadrupole LC/MS/MS system (Agilent Technologies, CA, USA) was employed for the analysis. For analysis of P3V8, chromatographic separation was achieved on a SunFire C8 Column (250 mm×4.6 mm, 5 μm). The mobile phase of water containing 0.2% formic acid (A) and acetonitrile (B) was used with a gradient elution (0-5 min, 20-70% B). The flow rate was 0.8 mL/min. Multiple reactions monitoring (MRM) with fragmentation transition of 500 to 129 in positive ion mode was employed for quantization of P3V8. For analysis of L1P3V8, Alltima Amino Alltech Column (250 mm×4.6 mm, 5 μm) was used for separation. Mobile phase of water (A) and acetonitrile (B) was used. The gradient elution for plasma samples was 0-4 min, 30-95% B, and for brain samples was 0-9 min, 10-95% B. The flow rate was 0.8 mL/min. MRM transition of 565 to 88 in positive ion mode was used for quantization of L1P3V8.

Data Analyses

Plasma concentration verse time profiles were analyzed by WinNonlin (Pharsight Corporation, Mountain View, Calif., USA, Version 2.1) to obtain the pharmacokinetics parameters. Other data were analyzed by one-way ANOVA followed by post hoc Tukey test or unpaired t-test. "*", "", "*" and "****" represent $P<0.05$, $P<0.01$, $P<0.001$ and $P<0.0001$ respectively, which are considered statistically significant.

All patents, patent applications, and other publications, including GenBank Accession Numbers, cited in this application are incorporated by reference in the entirety for all purposes.

TABLE 1

Binding affinity of P3WT and P3 variants toward expanded $MJD_{CAG78}$ RNA

| Peptide | Sequence | $K_D$ (μM) |
| --- | --- | --- |
| P3WT | Asp-Gly-Lys-Ser-Lys-Gly-Ile-Ala-Tyr-Ile-Glu-Phe-Lys (SEQ ID NO: 1) | 8.37 ± 3.83 |
| P3 variant 1 (P3V1) | Asp-(d-Ala)-Lys-Ser-Lys-Gly-Ile-Ala-Tyr-Ile-Glu-Phe-Lys (SEQ ID NO: 7) | 0.12 ± 0.04 |
| P3 variant 2 (P3V2) | Asp-Gly-Lys-Ser-Lys-Gly-Ile-Ala-Trp-Ile-Glu-Phe-Lys (SEQ ID NO: 8) | 2.21 ± 1.27 |
| P3 variant 3 (P3V3) | Asp-Gly-Lys-Ser-Lys-Gly-Ile-Ala-Tyr-Ile-Glu-Tyr-Lys (SEQ ID NO: 9) | 1.74 ± 0.67 |
| P3 variant 4 (P3V4) | Asp-Gly-Lys-Ser-Lys-Gly-Ile-Ala-Tyr-Ile-Glu-Trp-Lys (SEQ ID NO: 10) | 4.44 ± 0.47 |
| P3 variant 5 (P3V5) | Asp-Gly-Arg-Ser-Arg-Gly-Ile-Ala-Tyr-Ile-Glu-Phe-Lys (SEQ ID NO: 11) | 0.86 ± 0.17 |
| P3 variant 6 (P3V6) | Asp-Gly-Arg-Ser-Arg-Gly-Ile-Ala-Tyr-Ile-Glu-Phe-Arg (SEQ ID NO: 12) | 23.27 ± 2.78 |
| P3 variant 7 (P3V7) | Asp-Gly-Lys-Ser-Lys-Gly-Ile-Ala-Tyr-Ile-Glu-Phe-Lys-$NH_2$ (SEQ ID NO: 13) | 3.67 ± 0.26 |
| P3 variant 8 (P3V8) | Ac-Asp-Gly-Lys-Ser-Lys-Gly-Ile-Ala-Tyr-Ile-Glu-Phe-Lys-$NH_2$ (SEQ ID NO: 14) | 0.33 ± 0.04 |
| P3 variant 9 (P3V9) | Ac-Asp-Gly-Arg-Ser-Arg-Gly-Ile-Ala-Tyr-Ile-Glu-Phe-Lys-$NH_2$ (SEQ ID NO: 15) | 2.34 ± 0.49 |

P3WT or P3 variants (0.7 mM) were titrated into $MJD_{CAG78}$ RNA (0.5 μM) and the thermal titration data were fitted to the 'one binding site model' to determine the dissociation constant ($K_D$). Data are expressed as mean ± S.E.M. for at least 3 independent experiments.

TABLE 2

Stability of P3V8 and L1P3V8 in different biological matrices after incubation at 37° C.

| | | Pecentage of remained (%) | | | |
|---|---|---|---|---|---|
| | Incubation Conc. | Incubation for 1 hr | | Incubation for 3 hr | |
| | 9 ng/mL) | P3V8 | L1P3V8 | P3V8 | L1P3V8 |
| Plasma | 2000 | 20.7 ± 3.3 | 98.8 ± 5.0*** | <0.6# | 86.9 ± 5.5 |
| | 1000 | 8.6 ± 0.5 | 98.7 ± 3.9*** | <1.3# | 21.2 ± 1.5 |
| | 500 | <2.5# | 88.1 ± 4.9 | N/A | 73.8 ± 5.7 |
| Brain homoge-nate | 2000 | 3.3 ± 0.6 | 45.0 ± 3.5*** | <0.6# | 21.2 ± 3.0 |
| | 1000 | 4.0 ± 1.6 | 22.8 ± 1.2*** | <1.3# | 15.8 ± 0.7 |
| | 500 | <2.5# | <20# | N/A | <20# |

Stability of P3V8 and L1P3V8 in different biological matrices after incubation at 37° C.
Data are presented as mean ± S.E.M. for 5 independent experiments.
***Indicates P < 0.001, significant difference compared with P3V8.
Indicates the concentration was below the lowest limit of quantification (12.5 ng/mL for P3V8 and 100 ng/mL for L1P3V8).
N/A indicates not applicable.

TABLE 3

Comparison of pharmacokinetic parameters of P3V8 and L1P3V8 after intravenous or intranasal administrations at 3 μmol/kg

| | Intravenous administration | | Intranasal administration (Pre-treated with 0.5% chitosan) | |
|---|---|---|---|---|
| | P3V8 | L1P3V8 | P3V8 | L1P3V8 |
| $C_{max}$ (nmol/L) | 452 ± 22 | 10394 ± 1225*** | 12 ± 2 | 74 ± 13*** |
| $T_{max}$ (min) | 2 ± 0 | 2 ± 0 | 15 ± 4 | 18 ± 1 |
| $AUC_{0-last}$ (min * nmol/L) | 1212 ± 80 | 179470 ± 18874*** | 85 ± 32 | 2277 ± 558*** |
| $T_{1/2}$ (min) | N/A | 17 ± 4 | N/A | 37 ± 5 |

TABLE 4

Binding affinity of P3WT and P3 mutants toward expanded $MJD_{C4G78}$ RNA

| Peptide | Sequence | $K_D$ (μM) |
|---|---|---|
| P3WT | Asp-Gly-Lys-Ser-Lys-Gly-Ile-Ala-Tyr-Ile-Glu-Phe-Lys (SEQ ID NO: 1) | 8.37 ± 3.83 |
| P3MT1 | Asp-Gly-Ala-Ser-Lys-Gly-Ile-Ala-Tyr-Ile-Glu-Phe-Lys (SEQ ID NO: 2) | 31.27 ± 8.29 |
| P3MT2 | Asp-Gly-Lys-Ser-Ala-Gly-Ile-Ala-Tyr-Ile-Glu-Phe-Lys (SEQ ID NO: 3) | 100.60 ± 13.99 |
| P3MT3 | Asp-Gly-Lys-Ser-Lys-Gly-Ile-Ala-Ala-Ile-Glu-Phe-Lys (SEQ ID NO: 4) | 16.61 ± 2.83 |
| P3MT4 | Asp-Gly-Lys-Ser-Lys-Gly-Ile-Ala-Tyr-Ile-Glu-Ala-Lys (SEQ ID NO: 5) | 17.38 ± 5.19 |
| P3MT5 | Asp-Gly-Lys-Ser-Lys-Gly-Ile-Ala-Tyr-Ile-Glu-Phe-Ala (SEQ ID NO: 6) | 51.30 ± 13.12 |

P3WT or P3 mutants (0.7 mM) were titrated into $MJD_{C4G78}$ RNA (0.5 μM) and the thermal titration data were fitted to the 'one binding site model' to determine the dissociation constant ($K_D$). Data are expressed as mean ± S.E.M. for at least 3 independent experiments.

TABLE 5

Binding affinity of P3V14-19 toward expanded $MJD_{C4G78}$ RNA

| Peptide | Sequence | $K_D$ (μM) |
|---|---|---|
| P3WT | Asp-Gly-Lys-Ser-Lys-Gly-Ile-Ala-Tyr-Ile-Glu-Phe-Lys (SEQ ID NO: 1) | 8.37 ± 3.83 |
| P3 variant 14 (P3V14) | Ac-Asp-Gly-(hArg)-Ser-Lys-Gly-Ile-Ala-Tyr-Ile-Glu-Phe-Lys-NH2 (SEQ ID NO: 16) | No binding |
| P3 variant 15 (P3V15) | Ac-Asp-Gly-Lys-Ser-(hArg)-Gly-Ile-Ala-Tyr-Ile-Glu-Phe-Lys-NH2 (SEQ ID NO: 17) | No binding |
| P3 variant 16 (P3V16) | Ac-Asp-Gly-(Orn)-Ser-Lys-Gly-Ile-Ala-Tyr-Ile-Glu-Phe-Lys-NH2 (SEQ ID NO: 18) | No binding |
| P3 variant 17 (P3V17) | Ac-Asp-Gly-Lys-Ser-(Orn)-Gly-Ile-Ala-Tyr-Ile-Glu-Phe-Lys-NH2 (SEQ ID NO: 19) | No binding |

TABLE 5-continued

Binding affinity of P3V14-19 toward expanded MJD$_{CAG78}$ RNA

| Peptide | Sequence | $K_D$ (μM) |
|---|---|---|
| P3 variant 18 (P3V18) | Ac-Asp-Gly-(Dap)-Ser-Lys-Gly-Ile-Ala-Tyr-Ile-Glu-Phe-Lys-NH$_2$ (SEQ ID NO: 20) | No binding |
| P3 variant 19 (P3V19) | Ac-Asp-Gly-Lys-Ser-(Dap)-Gly-Ile-Ala-Tyr-Ile-Glu-Phe-Lys-NH$_2$ (SEQ ID NO: 21) | No binding |
| P3 variant 20 (P3V20) | Ac-Asp-Gly-Lys-Ser-Lys-Gly-Ile-Ala-Tyr-Ile-Glu-Phe-Lys-Asp-Gly-Lys-Ser-Lys-Gly-Ile-Ala-Tyr-Ile-Glu-Phe-Lys-NH$_2$ (SEQ ID NO: 22) | No binding |
| P3 variant 21 (P3V21) | Ac-Asp-Gly-Lys-Ser-Lys-Gly-Ile-Ala-Tyr-Ile-Glu-Phe-Lys-Gly-Asp-Gly-Lys-Ser-Lys-Gly-Ile-Ala-Tyr-Ile-Glu-Phe-Lys-NH$_2$ (SEQ ID NO: 23) | No binding |

P3WT or P3 variants (0.7 mM) were titrated into MJD$_{CAG78}$ RNA (0.5 μM) and the thermal titration data were fitted to the 'one binding site model' to determine the dissociation constant ($K_D$). Data are expressed as mean ± S.E.M. for at least 3 independent experiments.

TABLE 6

Binding affinity of P3V8 toward MJD$_{CAG27}$, MJD$_{CAG78}$, MJD$_{CAA/G78}$ RNA

| Peptide | RNA | $K_D$ (μM) |
|---|---|---|
| P3V8 | MJD$_{CAG27}$ RNA | 2.19 ± 0.27 |
| P3V8 | MJD$_{CAG78}$ RNA | 0.33 ± 0.04 |
| P3V8 | MJD$_{CAA/G78}$ RNA | 2.94 ± 0.96 |

P3V8 (0.7 mM) was titrated into MJD$_{CAG27/78}$ RNA or MJD$_{CAA/G78}$ RNA (0.5 μM).
The thermal titration data were fitted to the 'one binding site model' to determine the dissociation constant ($K_D$).
Data are expressed as mean ± S.E.M. for at least 3 independent experiments.

TABLE 7

Binding affinity of P3 and P3 variant toward expanded MJD$_{CAG78}$ RNA

| Peptide | Sequence | $K_D$ (μM) |
|---|---|---|
| P3WT | Asp-Gly-Lys-Ser-Lys-Gly-Ile-Ala-Tyr-Ile-Glu-Phe-Lys (SEQ ID NO: 1) | 8.37 ± 3.83 |
| P3 variant 10 (P3V10) | H-tPNA-Asp-Gly-Lys-Ser-Lys-Gly-Ile-Ala-Tyr-Ile-Glu-Phe-Lys-NH$_2$ (SEQ ID NO: 24) | 2.24 ± 0.10 |
| P3 variant 11 (P3V11) | H-tPNA-**-Lys-Ser-Lys-Gly-Ile-Ala-Tyr-Ile-Glu-Phe-Lys-NH$_2$ (SEQ ID NO: 25) | 0.12 ± 0.04 |
| P3 variant 12 (P3V12) | H-Asp-Gly-Lys-Ser-Lys-Gly-Ile-tPNA-*-Ile-Glu-Phe-Lys-NH$_2$ (SEQ ID NO: 26) | 9.93 ± 2.19 |
| P3 variant 13 (P3V13) | H-cPNA-gPNA-tPNA-Asp-Gly-Lys-Ser-*-Gly-Ile-Ala-Tyr-Ile-Glu-Phe-Lys-NH$_2$ (SEQ ID NO: 27) | 10.78 ± 3.08 |
| P3 variant 22 (P3V22) | H-Asp-Gly-Lys-Ser-Lys-Gly-Ile-Ala-Tyr-Ile-Glu-Phe-Lys-tPNA-NH$_2$ (SEQ ID NO: 28) | No binding |
| P3 variant 23 (P3V23) | H-Asp-Gly-Lys-Ser-Lys-Gly-Ile-Ala-Tyr-Ile-Glu-Phe-Lys-tPNA-cPNA-gPNA-NH$_2$ (SEQ ID NO: 29) | 233.00 ± 98.87 |
| P3 variant 24 (P3V24) | Hi-cPNA-**-Lys-Ser-Lys-Gly-Ile-Ala-Tyr-Ile-Glu-Phe-Lys-NH$_2$ (SEQ ID NO: 30) | 0.96 ± 0.14 |

TABLE 7-continued

Binding affinity of P3 and P3 variant toward expanded MJD$_{CAG78}$ RNA

| Peptide | Sequence | K$_D$ (µM) |
|---|---|---|
| P3 variant 25 (P3V25) | H-aPNA-**-Lys-Ser-Lys-Gly-Ile-Ala-Tyr-Ile-Glu-Phe-Lys-NH$_2$ (SEQ ID NO: 31) | 8.28 ± 2.27 |
| P3 variant 26 (P3V26) | H-gPNA-**-Lys-Ser-Lys-Gly-Ile-Ala-Tyr-Ile-Glu-Phe-Lys-NH$_2$ (SEQ ID NO: 32) | 8.85 ± 2.85 |
| P3 variant 27 (P3V27) | H-cptPNA-**-Lys-Ser-Lys-Gly-Ile-Ala-Tyr-Ile-Glu-Phe-Lys-NH$_2$ (SEQ ID NO: 33) | 11.23 ± 4.37 |

P3WT or P3 variants (0.7 mM) were titrated into MJD$_{CAG78}$ RNA (0.5 µM) and the thermal titration data were fitted to the 'one binding site model' to determine the dissociation constant (K$_D$). Data are expressed as mean ± S.E.M. for at least 3 independent experiments.

REFERENCES

1. Orr, H. T. & Zoghbi, H. Y. Trinucleotide repeat disorders. Annu. Rev. Neurosci. 30, 575-621 (2007).
2. Sakahira, H., Breuer, P., Hayer-Hartl, M. K. & Hartl, F. U. Molecular chaperones as modulators of polyglutamine protein aggregation and toxicity. Proc. Natl. Acad. Sci. USA 99(Suppl 4), 16412-16418 (2002).
3. Takahashi, T., Katada, S. & Onodera, O. Polyglutamine diseases: where does toxicity come from? what is toxicity? where are we going? J. Mol. Cell. Biol. 2, 180-191 (2010).
4. Michalik, A. & Van Broeckhoven, C. Pathogenesis of polyglutamine disorders: aggregation revisited. Hum. Mol. Genet. 12(Spec No. 2), R173-86 (2003).
5. Fiszer, A. & Krzyzosiak, W. J. RNA toxicity in polyglutamine disorders: concepts, models, and progress of research. J. Mol. Med. (Berl) 91, 683-691 (2013).
6. Fiszer, A. & Krzyzosiak, W. J. Oligonucleotide-based strategies to combat polyglutamine diseases. Nucleic Acids Res. 42, 6787-6810 (2014).
7. Li, L. B., Yu, Z., Teng, X. & Bonini, N. M. RNA toxicity is a component of ataxin-3 degeneration in Drosophila. Nature 453, 1107-1111 (2008).
8. Marti, E. RNA toxicity induced by expanded CAG repeats in Huntington's disease. Brain Pathol. 26, 779-786 (2016).
9. de Mezer, M., Wojciechowska, M., Napierala, M., Sobczak, K. & Krzyzosiak, W. J. Mutant CAG repeats of Huntingtin transcript fold into hairpins, form nuclear foci and are targets for RNA interference. Nucleic Acids Res. 39, 3852-3863 (2011).
10. Mykowska, A., Sobczak, K., Wojciechowska, M., Kozlowski, P. & Krzyzosiak, W. J. CAG repeats mimic CUG repeats in the misregulation of alternative splicing. Nucleic Acids Res. 39, 8938-8951 (2011).
11. Krol, J. et al. Ribonuclease dicer cleaves triplet repeat hairpins into shorter repeats that silence specific targets. Mol. Cell 25, 575-586 (2007).
12. Banez-Coronel, M. et al. A pathogenic mechanism in Huntington's disease involves small CAG-repeated RNAs with neurotoxic activity. PLoS Genet. 8, e1002481 (2012).
13. Tsoi, H., Lau, T. C., Tsang, S. Y., Lau, K. F. & Chan, H. Y. CAG expansion induces nucleolar stress in polyglutamine diseases. Proc. Natl. Acad. Sci. USA 109, 13428-13433 (2012).
14. Tsoi, H. & Chan, H. Y. Expression of expanded CAG transcripts triggers nucleolar stress in Huntington's disease. Cerebellum 12, 310-312 (2013).
15. James, A., Wang, Y., Raje, H., Rosby, R. & DiMario, P. Nucleolar stress with and without p53. Nucleus 5, 402-426 (2014).
16. Wang, D. B., Kinoshita, C., Kinoshita, Y. & Morrison, R. S. P53 and Mitochondrial Function in Neurons. Biochim. Biophys. Acta 1842, 1186-1197 (2014).
17. Zhang, Y. & Lu, H. Signaling to p53: ribosomal proteins find their way. Cancer. Cell. 16, 369-377 (2009).
18. Rickards, B., Flint, S. J., Cole, M. D. & LeRoy, G. Nucleolin is required for RNA polymerase I transcription in vivo. Mol. Cell. Biol. 27, 937-948 (2007).
19. Ginisty, H., Amalric, F. & Bouvet, P. Nucleolin functions in the first step of ribosomal RNA processing. EMBO J. 17, 1476-1486 (1998).
20. Bouvet, P., Diaz, J. J., Kindbeiter, K., Madjar, J. J. & Amalric, F. Nucleolin interacts with several ribosomal proteins through its RGG domain. J. Biol. Chem. 273, 19025-19029 (1998).
21. Zhang, Q. et al. Assessing a peptidylic inhibitor-based therapeutic approach that simultaneously suppresses polyglutamine RNA and protein-mediated toxicities in patient cells and Drosophila. Dis. Model. Mech. 9, 321-334 (2016).
22. Fujiwara, Y. et al. Structure and function of the N-terminal nucleolin binding domain of nuclear valosin-containing protein-like 2 (NVL2) harboring a nucleolar localization signal. J. Biol. Chem. 286, 21732-21741 (2011).
23. Shen, Y., Maupetit, J., Derreumaux, P. & Tuffery, P. Improved PEP-FOLD Approach for Peptide and Miniprotein Structure Prediction. J. Chem. Theory Comput. 10, 4745-4758, http://bioserv.rpbs.univ-paris-diderot.fr/services/PEP-FOLD/ (2014).
24. Knudsen, L. B. et al. Potent derivatives of glucagon-like peptide-1 with pharmacokinetic properties suitable for once daily administration. J. Med. Chem. 43, 1664-1669 (2000).
25. Madsen, K. et al. Structure-activity and protraction relationship of long-acting glucagon-like peptide-1 derivatives: importance of fatty acid length, polarity, and bulkiness. J. Med. Chem. 50, 6126-6132 (2007).
26. Oh, D. et al. Enhanced cellular uptake of short polyarginine peptides through fatty acylation and cyclization. Mol. Pharm. 11, 2845-2854 (2014).
27. Mittal, D. et al. Insights into direct nose to brain delivery: current status and future perspective. Drug Deliv. 21, 75-86 (2014).

28. Arispe, N., Diaz, J. C. & Flora, M. Efficiency of histidine-associating compounds for blocking the alzheimer's Abeta channel activity and cytotoxicity. Biophys. J. 95, 4879-4889 (2008).
29. Tawani, A. & Kumar, A. Structural Insights Reveal the Dynamics of the Repeating r(CAG) Transcript Found in Huntington's Disease (HD) and Spinocerebellar Ataxias (SCAs). PLoS One 10, e0131788 (2015).
30. Popiel, H. A. et al. The Aggregation Inhibitor Peptide QBP1 as a Therapeutic Molecule for the Polyglutamine Neurodegenerative Diseases. J. Amino Acids 2011, 265084 (2011).
31. Mishra, R. et al. Inhibiting the nucleation of amyloid structure in a huntingtin fragment by targeting alpha-helix-rich oligomeric intermediates. J. Mol. Biol. 415, 900-917 (2012).
32. Kazantsev, A. et al. A bivalent Huntingtin binding peptide suppresses polyglutamine aggregation and pathogenesis in Drosophila. Nat. Genet. 30, 367-376 (2002).
33. Arribat, Y. et al. A huntingtin peptide inhibits polyQ-huntingtin associated defects. PLoS One 8, e68775 (2013).
34. Kumar, A. et al. Chemical correction of pre-mRNA splicing defects associated with sequestration of muscleblind-like 1 protein by expanded r(CAG)-containing transcripts. ACS Chem. Biol. 7, 496-505 (2012).
35. van Witteloostuijn, S. B., Pedersen, S. L. & Jensen, K. J. Half-Life Extension of Biopharmaceuticals using Chemical Methods: Alternatives to PEGylation. Chem Med Chem 11, 2474-2495 (2016).
36. Tsoi, H., Lau, C. K., Lau, K. F. & Chan, H. Y. Perturbation of U2AF65/NXF1-mediated RNA nuclear export enhances RNA toxicity in polyQ diseases. Hum. Mol. Genet. 20, 3787-3797 (2011).
37. Lau, K. F. et al. Dexras1 interacts with FE65 to regulate FE65-amyloid precursor protein-dependent transcription. J. Biol. Chem. 283, 34728-34737 (2008).
38. Chau, K. W., Chan, W. Y., Shaw, P. C. & Chan, H. Y. Biochemical investigation of Tau protein phosphorylation status and its solubility properties in Drosophila. Biochem. Biophys. Res. Commun. 346, 150-159 (2006).
39. Wong, S. L., Chan, W. M. & Chan, H. Y. Sodium dodecyl sulfate-insoluble oligomers are involved in polyglutamine degeneration. FASEB J. 22, 3348-3357 (2008).
40. Schrodinger, L. L. C. The PyMOL Molecular Graphics System, Version 1.8. http://www.pymol.org (2015).

What is claimed is:

1. An isolated polypeptide consisting of the amino acid sequence of SEQ ID NO:1, wherein the C-terminus is amidated, and wherein the N-terminus is acetylated or lipidated.

2. The polypeptide of claim 1, which is acetylated at the N-terminus.

3. The polypeptide of claim 1, which is lipidated at the N-terminus.

4. The polypeptide of claim 3, which is lipidated with palmitic acid.

5. A composition comprising the polypeptide of claim 1 and a physiologically acceptable excipient.

6. The composition of claim 5, wherein the polypeptide consists of SEQ ID NO:1 with N-terminal acetylation and C-terminal amidation.

7. The composition of claim 5, wherein the polypeptide consists of SEQ ID NO:1 with N-terminal lipidation and C-terminal amidation.

8. The composition of claim 7, wherein the N-terminal lipidation is by palmitic acid.

9. The composition of claim 5, further comprising another therapeutic agent effective for treating a polyQ disease.

10. A kit for treating a polyQ disease, comprising a container containing the composition of claim 5.

11. The kit of claim 10, further comprising a second container containing another therapeutic agent effective for treating a polyQ disease.

12. The kit of claim 10, further comprising informational material providing instructions on administration of the composition.

13. A method for treating a polyQ disease in a subject, comprising administering to the subject an effective amount of a polypeptide of claim 1.

14. The method of claim 13, wherein the polypeptide consists of SEQ ID NO:1 with N-terminal acetylation and C-terminal amidation.

15. The method of claim 13, wherein another therapeutic agent effective for treating a polyQ disease is co-administered to the patient.

16. The method of claim 13, wherein the polypeptide consists of SEQ ID NO:1 with N-terminal lipidation and C-terminal amidation.

17. The method of claim 13, wherein the polypeptide is administered orally, intravenously, intramuscularly, intraperitoneally, or subcutaneously.

18. The method of claim 13, wherein the subject has been diagnosed with a polyQ disease or is at risk of developing a polyQ disease.

19. The method of claim 13, wherein the polypeptide is administered once daily, weekly, or monthly.

20. The method of claim 13, wherein about 1-10,000 mg, about 10-1,000 mg, about 10-100 mg, about 20-50 mg, or about 10, 20, 30, 40, or 50 mg of the polypeptide is administered each time to the subject per kg of the subject's body weight.

* * * * *

```
SEQUENCE LISTING

<160> NUMBER OF SEQ ID NOS: 34

<210> SEQ ID NO 1
<211> LENGTH: 13
<212> TYPE: PRT
<213> ORGANISM: Homo sapiens

<400> SEQUENCE: 1

Asp Gly Lys Ser Lys Gly Ile Ala Tyr Ile Glu Phe Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic construct

<400> SEQUENCE: 2

Asp Gly Ala Ser Lys Gly Ile Ala Tyr Ile Glu Phe Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic construct

<400> SEQUENCE: 3

Asp Gly Lys Ser Ala Gly Ile Ala Tyr Ile Glu Phe Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic construct

<400> SEQUENCE: 4
```

```
Asp Gly Lys Ser Lys Gly Ile Ala Ala Ile Glu Phe Lys
1               5                   10
```

<210> SEQ ID NO 5
<211> LENGTH: 13
<212> TYPE: PRT
<213> ORGANISM: Artificial Sequence
<220> FEATURE:
<223> OTHER INFORMATION: Synthetic construct

<400> SEQUENCE: 5

```
Asp Gly Lys Ser Lys Gly Ile Ala Tyr Ile Glu Ala Lys
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: Synthetic construct

<400> SEQUENCE: 6

```
Asp Gly Lys Ser Lys Gly Ile Ala Tyr Ile Glu Phe Ala
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = Ala in d-configuration

<400> SEQUENCE: 7

```
Asp Xaa Lys Ser Lys Gly Ile Ala Tyr Ile Glu Phe Lys
1               5                   10
```

<210> SEQ ID NO 8
<211> LENGTH: 13
<212> TYPE: PRT
<213> ORGANISM: Artificial Sequence
<220> FEATURE:
<223> OTHER INFORMATION: Synthetic construct

<400> SEQUENCE: 8

```
Asp Gly Lys Ser Lys Gly Ile Ala Trp Ile Glu Phe Lys
1               5                   10
```

<210> SEQ ID NO 9
<211> LENGTH: 13
<212> TYPE: PRT
<213> ORGANISM: Artificial Sequence
<220> FEATURE:
<223> OTHER INFORMATION: Synthetic construct

<400> SEQUENCE: 9

```
Asp Gly Lys Ser Lys Gly Ile Ala Tyr Ile Glu Tyr Lys
1               5                   10
```

<210> SEQ ID NO 10
<211> LENGTH: 13
<212> TYPE: PRT
<213> ORGANISM: Artificial Sequence
<220> FEATURE:
<223> OTHER INFORMATION: Synthetic construct

```
<400> SEQUENCE: 10

Asp Gly Lys Ser Lys Gly Ile Ala Tyr Ile Glu Trp Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Synthetic construct

<400> SEQUENCE: 11

Asp Gly Arg Ser Arg Gly Ile Ala Tyr Ile Glu Phe Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic construct

<400> SEQUENCE: 12

Asp Gly Arg Ser Arg Gly Ile Ala Tyr Ile Glu Phe Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 13

Asp Gly Lys Ser Lys Gly Ile Ala Tyr Ile Glu Phe Xaa
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 14

Xaa Gly Lys Ser Lys Gly Ile Ala Tyr Ile Glu Phe Xaa
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 15

Xaa Gly Arg Ser Arg Gly Ile Ala Tyr Ile Glu Phe Xaa
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (3)..(3)
<223> OTHER INFORMATION: Xaa = homoarginine
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 16

Xaa Gly Xaa Ser Lys Gly Ile Ala Tyr Ile Glu Phe Xaa
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (5)..(5)
<223> OTHER INFORMATION: Xaa = homoarginine
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 17

Xaa Gly Lys Ser Xaa Gly Ile Ala Tyr Ile Glu Phe Xaa
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (3)..(3)
<223> OTHER INFORMATION: Xaa = Ornithine
<220> FEATURE:
<221> NAME/KEY: MISC_FEATURE
```

<222> LOCATION: (13)..(13)
<223> OTHER INFORMATION: Xaa = Lys with C-terminal amidation

<400> SEQUENCE: 18

Xaa Gly Xaa Ser Lys Gly Ile Ala Tyr Ile Glu Phe Xaa
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (5)..(5)
<223> OTHER INFORMATION: Xaa = Ornithine
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 19

Xaa Gly Lys Ser Xaa Gly Ile Ala Tyr Ile Glu Phe Xaa
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (3)..(3)
<223> OTHER INFORMATION: Xaa = 2,3-diaminopropionic acid
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 20

Xaa Gly Xaa Ser Lys Gly Ile Ala Tyr Ile Glu Phe Xaa
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (5)..(5)
<223> OTHER INFORMATION: Xaa = 2,3-diaminopropionic acid
<220> FEATURE:
<221> NAME/KEY: MISC_FEATURE
<222> LOCATION: (13)..(13)
<223> OTHER INFORMATION: Xaa = Lys with C-terminal amidation

<400> SEQUENCE: 21

```
Xaa Gly Lys Ser Xaa Gly Ile Ala Tyr Ile Glu Phe Xaa
1               5                   10
```

<210> SEQ ID NO 22
<211> LENGTH: 26
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (26)..(26)
<223> OTHER INFORMATION: Xaa = Lys with C-terminal amidation

<400> SEQUENCE: 22

```
Xaa Gly Lys Ser Lys Gly Ile Ala Tyr Ile Glu Phe Lys Asp Gly Lys
1               5                   10                  15

Ser Lys Gly Ile Ala Tyr Ile Glu Phe Xaa
            20                  25
```

<210> SEQ ID NO 23
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal acetylation
<220> FEATURE:
<221> NAME/KEY: MISC_FEATURE
<222> LOCATION: (27)..(27)
<223> OTHER INFORMATION: Xaa = Lys with C-terminal amidation

<400> SEQUENCE: 23

```
Xaa Gly Lys Ser Lys Gly Ile Ala Tyr Ile Glu Phe Lys Gly Asp Gly
1               5                   10                  15

Lys Ser Lys Gly Ile Ala Tyr Ile Glu Phe Xaa
            20                  25
```

<210> SEQ ID NO 24
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Thymine base linked to a backbone of
      N-(2-aminoethyl)-glycine (tPNA). N-terminal amino group replaced
      by hydrogen.
<220> FEATURE:
<221> NAME/KEY: MISC_FEATURE
<222> LOCATION: (14)..(14)
<223> OTHER INFORMATION: Xaa = Lys with C-terminal amidation

<400> SEQUENCE: 24

```
Xaa Asp Gly Lys Ser Lys Gly Ile Ala Tyr Ile Glu Phe Xaa
1               5                   10
```

<210> SEQ ID NO 25
<211> LENGTH: 12
<212> TYPE: PRT

```
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Thymine base linked to a backbone of
      N-(2-aminoethyl)-glycine (tPNA). N-terminal amino group replaced
      by hydrogen.
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 25

Xaa Lys Ser Lys Gly Ile Ala Tyr Ile Glu Phe Xaa
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal amino group replaced
      by hydrogen.
<220> FEATURE:
<221> NAME/KEY: MISC_FEATURE
<222> LOCATION: (8)..(8)
<223> OTHER INFORMATION: Xaa = Thymine base linked to a backbone of
      N-(2-aminoethyl)-glycine (tPNA)
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 26

Xaa Gly Lys Ser Lys Gly Ile Xaa Ile Glu Phe Xaa
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Cytosine base linked to a backbone of
      N-(2-aminoethyl)-glycine (cPNA). N-terminal amino group replaced
      by hydrogen.
<220> FEATURE:
<221> NAME/KEY: MISC_FEATURE
<222> LOCATION: (2)..(2)
<223> OTHER INFORMATION: Xaa = Guanine base linked to a backbone of
      N-(2-aminoethyl)-glycine (gPNA)
<220> FEATURE:
<221> NAME/KEY: MISC_FEATURE
<222> LOCATION: (3)..(3)
<223> OTHER INFORMATION: Xaa = Thymine base linked to a backbone of
      N-(2-aminoethyl)-glycine (tPNA)
<220> FEATURE:
<221> NAME/KEY: MISC_FEATURE
<222> LOCATION: (15)..(15)
<223> OTHER INFORMATION: Xaa = Lys with C-terminal amidation

<400> SEQUENCE: 27

Xaa Xaa Xaa Asp Gly Lys Ser Gly Ile Ala Tyr Ile Glu Phe Xaa
1               5                   10                  15
```

```
<210> SEQ ID NO 28
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal amino group replaced
      by hydrogen.
<220> FEATURE:
<221> NAME/KEY: MISC_FEATURE
<222> LOCATION: (14)..(14)
<223> OTHER INFORMATION: Xaa = Thymine base linked to a backbone of
      N-(2-aminoethyl)-glycine (tPNA) with C-terminal amidation

<400> SEQUENCE: 28

Xaa Gly Lys Ser Lys Gly Ile Ala Tyr Ile Glu Phe Lys Xaa
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp with N-terminal amino group replaced
      by hydrogen.
<220> FEATURE:
<221> NAME/KEY: MISC_FEATURE
<222> LOCATION: (14)..(14)
<223> OTHER INFORMATION: Xaa = Thymine base linked to a backbone of
      N-(2-aminoethyl)-glycine (tPNA)
<220> FEATURE:
<221> NAME/KEY: MISC_FEATURE
<222> LOCATION: (15)..(15)
<223> OTHER INFORMATION: Xaa = Cytosine base linked to a backbone of
      N-(2-aminoethyl)-glycine (cPNA)
<220> FEATURE:
<221> NAME/KEY: MISC_FEATURE
<222> LOCATION: (16)..(16)
<223> OTHER INFORMATION: Xaa = Guanine base linked to a backbone of
      N-(2-aminoethyl)-glycine (gPNA) with C-terminal amidation

<400> SEQUENCE: 29

Xaa Gly Lys Ser Lys Gly Ile Ala Tyr Ile Glu Phe Lys Xaa Xaa Xaa
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Cytosine base linked to a backbone of
      N-(2-aminoethyl)-glycine (cPNA). N-terminal amino group replaced
      by hydrogen.
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 30

Xaa Lys Ser Lys Gly Ile Ala Tyr Ile Glu Phe Xaa
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Adenine base linked to a backbone of
      N-(2-aminoethyl)-glycine (aPNA). N-terminal amino group replaced
      by hydrogen.
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 31

Xaa Lys Ser Lys Gly Ile Ala Tyr Ile Glu Phe Xaa
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Guanine base linked to a backbone of
      N-(2-aminoethyl)-glycine (gPNA). N-terminal amino group replaced
      by hydrogen.
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 32

Xaa Lys Ser Lys Gly Ile Ala Tyr Ile Glu Phe Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = cPNA-gPNA-tPNA. N-terminal amino group
      replaced by hydrogen.
<220> FEATURE:
<221> NAME/KEY: MISC_FEATURE
<222> LOCATION: (12)..(12)
<223> OTHER INFORMATION: Xaa = Lys with C-terminal amidation

<400> SEQUENCE: 33

Xaa Lys Ser Lys Gly Ile Ala Tyr Ile Glu Phe Xaa
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic construct

```
<400> SEQUENCE: 34

Ser Asn Trp Lys Trp Trp Pro Gly Ile Phe Asp
1               5                   10
```